United States Patent
Zankel et al.

(10) Patent No.: US 11,505,550 B2
(45) Date of Patent: Nov. 22, 2022

(54) ADO-RESISTANT CYSTEAMINE ANALOGS AND USES THEREOF

(71) Applicant: HORIZON ORPHAN LLC, Lake Forest, IL (US)

(72) Inventors: Todd C. Zankel, San Francisco, CA (US); John Unitt, Nottingham (GB); Timothy Phillips, Nottingham (GB); Benoit Gourdet, Nottingham (GB); Lorna Duffy, Nottingham (GB)

(73) Assignee: HORIZON ORPHAN LLC, Lake Forest, IL (US)

( * ) Notice: Subject to any disclaimer, the term of this patent is extended or adjusted under 35 U.S.C. 154(b) by 0 days.

(21) Appl. No.: 17/164,428

(22) Filed: Feb. 1, 2021

(65) Prior Publication Data
US 2022/0024920 A1    Jan. 27, 2022

Related U.S. Application Data

(62) Division of application No. 15/201,969, filed on Jul. 5, 2016, now Pat. No. 10,906,904.

(60) Provisional application No. 62/387,337, filed on Dec. 23, 2015, provisional application No. 62/187,939, filed on Jul. 2, 2015.

(51) Int. Cl.
| | |
|---|---|
| *C07C 323/30* | (2006.01) |
| *C07D 211/54* | (2006.01) |
| *C07C 323/26* | (2006.01) |
| *C07D 211/60* | (2006.01) |
| *C07D 471/08* | (2006.01) |
| *A61K 31/145* | (2006.01) |
| *A61K 31/4402* | (2006.01) |
| *A61K 31/4465* | (2006.01) |
| *A61K 31/40* | (2006.01) |
| *A61K 31/4409* | (2006.01) |
| *A61K 31/445* | (2006.01) |
| *A61K 31/397* | (2006.01) |
| *C07C 323/25* | (2006.01) |
| *C07D 205/04* | (2006.01) |
| *C07D 207/08* | (2006.01) |
| *C07D 213/32* | (2006.01) |
| *C07D 213/70* | (2006.01) |
| *C07D 223/06* | (2006.01) |
| *C07D 295/088* | (2006.01) |
| *C07D 451/04* | (2006.01) |

(52) U.S. Cl.
CPC .......... *C07D 471/08* (2013.01); *A61K 31/145* (2013.01); *A61K 31/397* (2013.01); *A61K 31/40* (2013.01); *A61K 31/4402* (2013.01); *A61K 31/445* (2013.01); *A61K 31/4409* (2013.01); *A61K 31/4465* (2013.01); *C07C 323/25* (2013.01); *C07C 323/26* (2013.01); *C07C 323/30* (2013.01); *C07D 205/04* (2013.01); *C07D 207/08* (2013.01); *C07D 211/54* (2013.01); *C07D 211/60* (2013.01); *C07D 213/32* (2013.01); *C07D 213/70* (2013.01); *C07D 223/06* (2013.01); *C07D 295/088* (2013.01); *C07D 451/04* (2013.01); *C07C 2601/04* (2017.05)

(58) Field of Classification Search
CPC ..... C07D 211/00; C07D 211/54; C07C 13/06; C07C 211/35
See application file for complete search history.

(56) References Cited

U.S. PATENT DOCUMENTS

| | | | |
|---|---|---|---|
| 2,809,918 | A | 10/1957 | Hermelin |
| 2,834,785 | A | 5/1958 | Biel et al. |
| 3,835,221 | A | 9/1974 | Fulberth et al. |
| 4,301,146 | A | 11/1981 | Sanvordeker |
| 4,432,966 | A | 2/1984 | Zeitoun et al. |
| 4,617,377 | A | 10/1986 | Corbet et al. |
| 4,728,512 | A | 3/1988 | Mehta et al. |
| 4,735,952 | A | 4/1988 | Ueda et al. |
| 4,794,001 | A | 12/1988 | Mehta et al. |
| 4,968,705 | A | 11/1990 | Regnier et al. |
| 4,988,689 | A | 1/1991 | Janssens et al. |
| 5,071,846 | A | 12/1991 | Janssens et al. |
| 5,126,356 | A | 6/1992 | Regnier et al. |
| 5,151,424 | A | 9/1992 | Janssens et al. |
| 5,153,207 | A | 10/1992 | Ito et al. |
| 5,217,980 | A | 6/1993 | Janssens et al. |
| 5,225,202 | A | 7/1993 | Hodges et al. |
| 5,272,150 | A | 12/1993 | Janssens et al. |
| 5,278,165 | A | 1/1994 | Janssens et al. |
| 5,317,025 | A | 5/1994 | Bru-Magniez et al. |
| 5,393,769 | A | 2/1995 | Oida et al. |
| 5,532,255 | A | 7/1996 | Raddatz et al. |

(Continued)

FOREIGN PATENT DOCUMENTS

| | | |
|---|---|---|
| BR | 9806353 A | 6/2000 |
| DE | 3808678 A1 | 9/1989 |

(Continued)

OTHER PUBLICATIONS

Apffel et al., Tumor rejection in experimental animals treated with radioprotective thiols, Cancer Res., 3592):429-37 (1975).

(Continued)

*Primary Examiner* — Theodore R. Howell
*Assistant Examiner* — George W Kosturko
(74) *Attorney, Agent, or Firm* — Global Patent Group, LLC; Cynthia Hathaway

(57) ABSTRACT

The present disclosure is directed to methods for treating diseases for which cysteamine is indicated and compounds useful in such methods.

2 Claims, 1 Drawing Sheet

(56) References Cited

U.S. PATENT DOCUMENTS

| | | | |
|---|---|---|---|
| 5,554,655 A | 9/1996 | Thoene | |
| 5,646,289 A | 7/1997 | Alt et al. | |
| 5,659,043 A | 8/1997 | Hayashi et al. | |
| 5,783,703 A | 7/1998 | Hayashi et al. | |
| 5,854,268 A | 12/1998 | Baker et al. | |
| 5,998,440 A | 12/1999 | Castro Pineiro et al. | |
| 6,127,388 A | 10/2000 | Bourrain et al. | |
| 6,297,260 B1* | 10/2001 | Bandarage | A61P 1/00 549/12 |
| 6,369,243 B1 | 4/2002 | MacMillan et al. | |
| 6,429,213 B1 | 8/2002 | Xue et al. | |
| 6,455,573 B1 | 9/2002 | Pinto et al. | |
| 6,479,478 B1 | 11/2002 | Abe et al. | |
| 6,632,823 B1 | 10/2003 | Vernier et al. | |
| 6,790,860 B2 | 9/2004 | Aebi et al. | |
| 6,858,626 B2 | 2/2005 | Xue et al. | |
| 7,189,756 B2 | 3/2007 | Aebi et al. | |
| 7,348,341 B2 | 3/2008 | Sanganee et al. | |
| 7,375,251 B2 | 5/2008 | Allegrini et al. | |
| 7,408,067 B2 | 8/2008 | Astles et al. | |
| 7,608,629 B2 | 10/2009 | Blanco-Pillado et al. | |
| 7,875,630 B2 | 1/2011 | Breen et al. | |
| 8,026,285 B2 | 9/2011 | Bezwada | |
| 8,119,623 B2 | 2/2012 | Burdack et al. | |
| 8,129,433 B2 | 3/2012 | Dohil et al. | |
| 8,207,191 B2 | 6/2012 | Forth et al. | |
| 8,222,411 B2 | 7/2012 | Feng et al. | |
| 8,263,636 B2 | 9/2012 | Ansorge et al. | |
| 8,394,372 B2 | 3/2013 | Andersson et al. | |
| 8,536,160 B2 | 9/2013 | Cerri et al. | |
| 8,546,407 B2 | 10/2013 | Berdini et al. | |
| 8,557,844 B2 | 10/2013 | Platt et al. | |
| 8,574,569 B2 | 11/2013 | Andersson et al. | |
| 8,785,439 B2 | 7/2014 | Kadereit et al. | |
| 8,809,336 B2 | 8/2014 | Berdini et al. | |
| 8,846,711 B2 | 9/2014 | Gerusz et al. | |
| 9,006,430 B2 | 4/2015 | Berdini et al. | |
| 9,051,321 B2 | 6/2015 | Gerusz et al. | |
| 10,906,904 B2 | 2/2021 | Zankel et al. | |
| 2003/0139427 A1 | 7/2003 | Castelhano et al. | |
| 2004/0209959 A1 | 10/2004 | Hogestatt et al. | |
| 2005/0245433 A1 | 11/2005 | Chan et al. | |
| 2006/0276502 A1 | 12/2006 | Stromblad et al. | |
| 2008/0027035 A1 | 1/2008 | Edwards et al. | |
| 2009/0048154 A1 | 2/2009 | Chan et al. | |
| 2009/0163705 A1 | 6/2009 | Manoharan et al. | |
| 2010/0022620 A1 | 1/2010 | Crispin et al. | |
| 2011/0070272 A1 | 3/2011 | Chan et al. | |
| 2011/0195929 A1 | 8/2011 | De Moor et al. | |
| 2011/0237538 A1 | 9/2011 | De Moor et al. | |
| 2012/0165304 A1 | 6/2012 | Mueller et al. | |
| 2012/0189546 A1 | 7/2012 | Graham et al. | |
| 2013/0323836 A1 | 12/2013 | Manoharan et al. | |

FOREIGN PATENT DOCUMENTS

| | | |
|---|---|---|
| DE | 102008032561 A1 | 1/2009 |
| EP | 151826 A1 | 8/1985 |
| EP | 157609 A2 | 10/1985 |
| EP | 339406 A1 | 11/1989 |
| EP | 399414 A1 | 11/1990 |
| GB | 780027 A | 7/1957 |
| GB | 2206879 A | 1/1989 |
| JP | H03118319 A | 5/1991 |
| JP | H09278776 A | 10/1997 |
| JP | 11043792 | 2/1999 |
| JP | 2001131067 A | 5/2001 |
| JP | 2003183280 A | 7/2003 |
| JP | 2003183281 A | 7/2003 |
| JP | 3724854 B2 | 12/2005 |
| JP | 2006001841 A | 1/2006 |
| JP | 04334357 B2 | 9/2009 |
| JP | 2014-508758 A | 4/2014 |
| WO | WO-92/04342 A1 | 3/1992 |
| WO | WO-93/06832 A1 | 4/1993 |
| WO | WO-96/04274 A1 | 2/1996 |
| WO | WO-99/36403 A1 | 7/1999 |
| WO | WO-00/21565 A1 | 4/2000 |
| WO | WO-02/08185 | 1/2002 |
| WO | WO-2005/014524 A2 | 2/2005 |
| WO | WO-2005/039548 A2 | 5/2005 |
| WO | WO-2007/079670 A1 | 7/2007 |
| WO | WO-2007/089670 A2 | 8/2007 |
| WO | WO-2008/128919 A2 | 10/2008 |
| WO | WO-2009/070781 A1 | 6/2009 |
| WO | WO-2009/121812 A1 | 10/2009 |
| WO | WO-201 0/029313 A1 | 3/2010 |
| WO | WO-2010/026113 A1 | 3/2010 |
| WO | WO-2010/041964 A1 | 4/2010 |
| WO | WO-2010/049678 A2 | 5/2010 |
| WO | WO-2012/055826 A1 | 5/2012 |
| WO | WO-2012/113079 A1 | 8/2012 |
| WO | WO-2013/024376 A1 | 2/2013 |
| WO | WO-2013/062544 A1 | 5/2013 |
| WO | WO-2013/078335 A1 | 5/2013 |
| WO | WO-2013083541 A1 * | 6/2013 ........... A61K 31/445 |
| WO | WO-2015/069888 A2 | 5/2015 |
| WO | WO-2015/150472 A2 | 10/2015 |
| WO | WO-2015/179308 A1 | 11/2015 |
| WO | WO-2016/046524 A1 | 3/2016 |

OTHER PUBLICATIONS

Becker et al., Why do so many drugs for Alzheimer's disease fail in development? J. Alzheimer's Disease, vol. 15, pp. 303-325 published 2008.

Belayev et al., Posttreatment with high-dose albumin reduces histopathological damage and improves neurological deficit following fluid percussion brain injury in rats, J. Neurotrauma, 16(6):445-53 (1999).

Bove et al., Neurotoxin-based models of Parkinson's disease, Neuroscience, 211:51-76 (2012).

Butler et al., Depletion of cystine in cystinotic fibroblasts by drugs enclosed in liposomes, Pediatr. Res., 12(1):46-51 (1978).

Carroll et al., Raptor Pharmaceuticals, published online Apr. 10, 2014.

CAS Registry Notes of 3772-62-1 in Korant WO 2000/021565 (2018).

Choudary et al., Synthesis of the Pleuromutilin Antibiotic SB-268091: A New Practical and Efficient Synthesis of Quinuclidine-4-thiol, Org. Process Res. Dev., 16(12):1927-39 (2012).

Coloso et al., Cysteamine dioxygenase: evidence for the physiological conversion of cysteamine to hypotaurine in rat and mouse tissues, Adv. Exp. Med. Biol., 583:25-36 (2006).

De Ferreyra et al., Therapeutic effectiveness of cystamine and cysteine to reduce liver cell necrosis induced by several hepatotoxins, Toxicol. Appl. Pharmacol., 48(2):221-8 (1979).

Dohil et al., Understanding intestinal cysteamine bitartrate absorption, J. Pediatr., 148(6):764-9 (2006).

Dominy et al., Discovery and characterization of a second mammalian thiol dioxygenase, cysteamine dioxygenase, J. Biol. Chem., 282(35):25189-98 (2007).

Eddy et al., Investigating mechanisms of chronic kidney disease in mouse models, Pediatr. Nephrol., 27(8):1233-47 (2012).

Fix, Strategies for delivery of peptides utilizing absorption-enhancing agents, J. Pharm. Sci., 85(12):1282-5 (1996).

Gahl et al., Cystinosis, N. Engl. J. Med., 347(2):111-21 (2002).

Gasparini et al., Peripheral markers in testing pathophysiological hypotheses and diagnosing Alzheimer's disease, FASEB J., 12(1):17-34 (1998).

Goodhart et al., An evaluation of aqueous film-forming dispersions for controlled release, Pharm. Tech., pp. 64-71 (Apr. 1984).

Greicius et al., J. Neurol. Neurosurg. Psychiatry, 72(6):691-70 (2002).

Hanafy et al., Antioxidant strategies in neurocritical care, Neurotherapeutics, 9(1):44-55 (2012).

International Search Report and Written Opinion, International Application No. PCT/US2016/040637, dated Nov. 25, 2016.

(56) References Cited

OTHER PUBLICATIONS

Invitation to Pay Additional Fees and, Where Applicable, Protest Fee, International Application No. PCT/US2016/040637, dated Sep. 19, 2016.

Irie, Influence of the radiation protective agents on the therapeutical effects of radiation for malignant tissues, Chemotherapia (Switzerland), 3:176-188 (1961) [Introduction only].

Karpuj et al., Evidence for a role for transglutaminase in Huntington's disease and the potential therapeutic implications, Neurochem. Int., 40(1):31-6 (2002).

Macdonald et al., Thioesters for the in vitro evaluation of agents to image brain cholinesterases, J. Enzyme Inhib. Med. Chem., 28(3):447-55 (2013).

Mitchell et al., Acetaminophen-induced hepatic injury: protective role of glutathione in man and rationale for therapy, Clin. Pharmacol. Ther., 16(4):676-84 (1974).

Oliyai et al., Prodrugs of peptides and proteins for improved formulation and delivery, Annu. Rev. Pharmacol. Toxicol., 33:521-44 (1993).

Piper et al., The use of alpha-amino acids in the synthesis of derivatives of 2-aminoethanethiol as potential antiradiation agents, J. Med. Chem., 9(6):911-20 (1966).

Prescott et al., Cysteamine or N-acetylcysteine for paracetamol poisoning?, Br. Med. J., 1(6116):856-7 (1978).

Prescott, Haemodialysis in paracetomol self-poisoning, Lancet, 2(7778):652 (1972).

Qiu et al., Cystamine ameliorates liver fibrosis induced by carbon tetrachloride via inhibition of tissue transglutaminase, World J. Gastroenterol., 13(32):4328-32 (2007).

Rao et al., A Convenient Preparation of 1-Mercapto-3-azidocyclobutane from 1,1-Cyclobutanedicarboxylic Acid, Synthetic Commun., 23(20):2915-20 (1993).

Richeldi et al., Efficacy of a tyrosine kinase inhibitor in idiopathic pulmonary fibrosis, N. Engl. J. Med., 365(12):1079-87 (2011).

Richerson et al., Cysteamine dioxygenase, Methods Enzymol., 143:410-5 (1987).

Russian Patent Application No. 2018103901, Office Action, dated May 28, 2021.

Shih et al., Cystine/glutamate exchange modulates glutathione supply for neuroprotection from oxidative stress and cell proliferation, J. Neurosci., 26(41):10514-23 (2006).

Tong, Characterization of Cysteine-34 in Serum Albumin, Dissertation, Presented in Partial Fulfillment of the Requirements for the Degree Doctor of Philosophy in the Graduate School of the Ohio State University (2003).

Tyukavkina et al., Bioorganic Chemistry, Second Edition (revised and supplemented), Medicine, 528 pp., see p. 495 (1991).

Van Bekkum et al., The radioprotective action of a number of cysteamine derivatives and related compounds, Int. J. Rad. Biol., 7(5):473-479 (1963).

Zhang et al., Genetics, vol. 203, pp. 509-609, published Mar. 17, 2016.

* cited by examiner

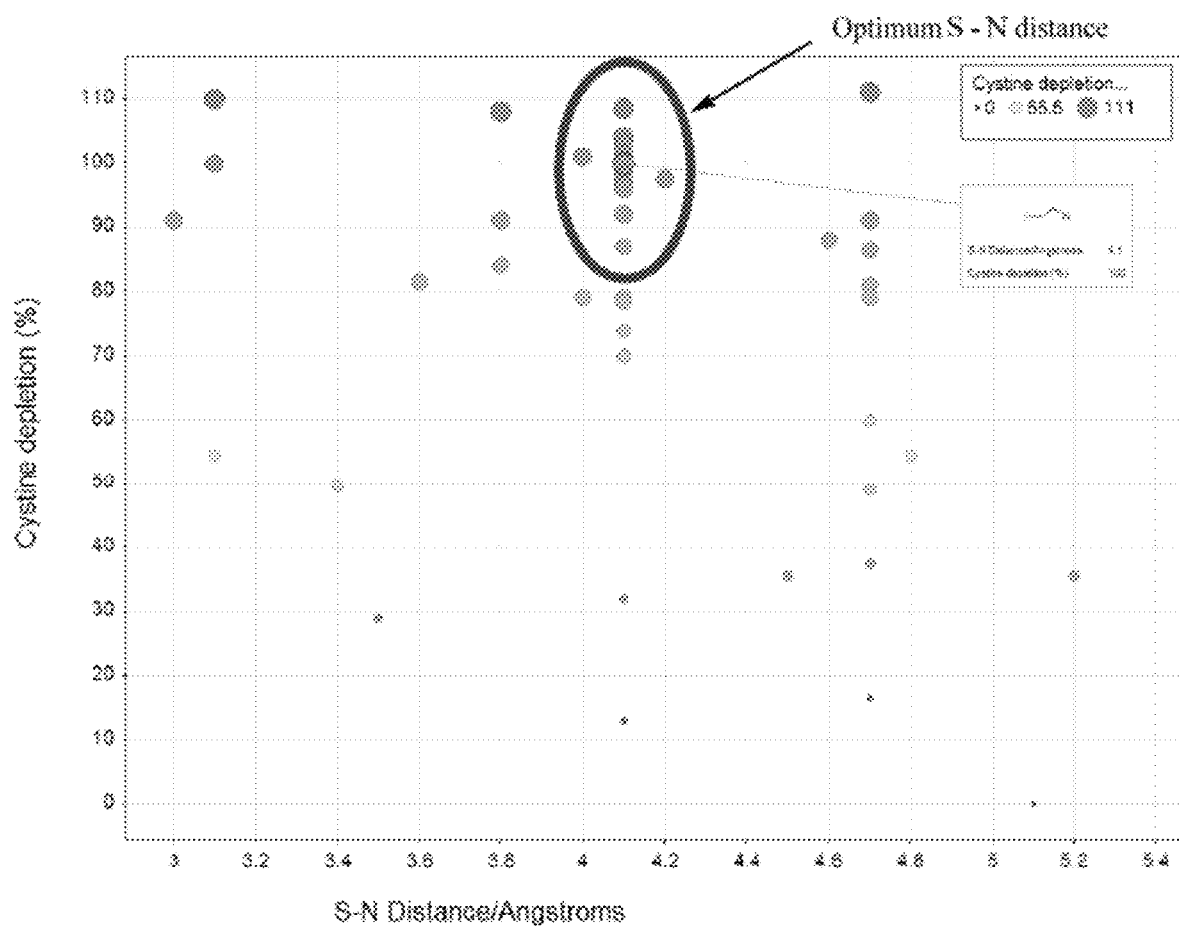

ADO-RESISTANT CYSTEAMINE ANALOGS AND USES THEREOF

CROSS-REFERENCE TO RELATED APPLICATIONS

This application is a divisional of U.S. application Ser. No. 15/201,969, which claims the benefit of U.S. Provisional Application No. 62/187,939, filed Jul. 2, 2015, and U.S. Provisional Application No. 62/387,337, filed Dec. 23, 2015, each of which is incorporated herein by reference in its entirety.

FIELD OF THE DISCLOSURE

The disclosure relates to materials and methods to treat diseases in which therapy with cysteamine is indicated. In particular, the disclosure provides therapeutic methods involving administration to a patient of a compound as disclosed herein.

BACKGROUND

Cysteamine (HS-CH2-CH2-NH2) is a small sulfhydryl compound that is able to cross cell membranes easily due to its small size. Cysteamine is currently FDA approved for use in the treatment of cystinosis, an intra-lysosomal cystine storage disorder. In cystinosis, cysteamine acts by converting cystine to cysteine and cysteine-cysteamine mixed disulfide, which are then both able to leave the lysosome through the cysteine and lysine transporters respectively (Gahl et al., N Engl J Med 347(2):111-21, 2002). Within the cytosol, the mixed disulfide can be reduced by its reaction with glutathione and the cysteine released can be used for further GSH synthesis. Treatment with cysteamine has been shown to result in lowering of intracellular cystine levels in circulating leukocytes (Dohil et al., J. Pediatr 148(6):764-9, 2006).

Cysteamine is converted to hypotaurine by cysteamine dioxygenase (ADO) (Coloso et al. (2006) Adv Exp Med Biol 583, 25-36; Dominy et al. (2007) J Biol Chem 282, 25189-25198; Richerson et al. (1987) Methods Enzymol 143, 410-415) and then ultimately to taurine, the most common amino acid in the body. Cysteamine is also discussed in Prescott et al., (Lancet 2(7778):652, 1979); Prescott et al., (Br Med J 1(6116):856-7, 1978); Mitchell et al., (Clin Pharmacol Ther 16(4):676-84, 1974); de Ferreyra et al., (Toxicol Appl Pharmacol. 48(2):221-8, 1979); and Qiu et al., (World J Gastroenterol. 13:4328-32, 2007). Unfortunately, the sustained concentrations of cysteamine necessary for therapeutic effect are difficult to maintain due to rapid metabolism and clearance of cysteamine from the body, with nearly all administered cysteamine converted to taurine in a matter of hours. These difficulties are transferred to patients in the form of high dosing levels and frequencies, with all of the consequent unpleasant side effects associated with cysteamine (e.g., gastrointestinal distress and body odor). See the package insert for CYSTAGON® (cysteamine bitartrate). International Publication No. WO 2007/079670 and U.S. Pat. Nos. 8,026,2854 and 8,129,433 disclose enterically coated cysteamine products and a method of reducing dosing frequency of cysteamine.

Cysteamine is addressed in International Patent Application Nos. WO 2009/070781, and WO 2007/089670, and U.S. Patent Publication Nos. 20110070272, 20090048154, and 20050245433.

SUMMARY

The present disclosure provides methods of treating a patient suffering from a disease for which treatment with cysteamine is indicated. The methods comprise administering to the patient an effective amount of a composition comprising a compound as disclosed herein. It is contemplated that administration of the composition reduces levels of cystine in patients, which can improve the detrimental effects of elevated cystine levels.

Suitable compositions comprise a compound of formula I or a disulfide thereof:

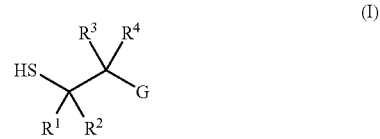

(I)

wherein:

$R^1$ and $R^2$ are independently selected from the group consisting of H and $C_{1-5}$alkyl; or $R^1$ and $R^2$, taken together with the carbon atom to which they are attached, form a 3-, 4-, 5-, 6-, 7-, or 8-membered carbocyclic ring;

$R^3$ and $R^4$ are independently selected from the group consisting of H and $C_{1-5}$alkyl; or $R^3$ and $R^4$, taken together with the carbon atom to which they are attached, form a 3-, 4-, 5-, 6-, 7-, or 8-membered carbocyclic ring;

G is selected from the group consisting of —$NR^5R^6$ and —$CR^7R^8NR^5R^6$;

$R^5$ and $R^6$ are independently selected from the group consisting of H and $C_{1-5}$alkyl; or $R^5$ and $R^6$, taken together with the nitrogen atom to which they are attached, form a 3-, 4-, 5-, 6-, 7-, or 8-membered heterocyclic ring;

$R^7$ and $R^8$ are independently selected from the group consisting of H and $C_{1-5}$alkyl; or $R^7$ and $R^8$, taken together with the carbon atom to which they are attached, form a 3-, 4-, 5-, 6-, 7-, or 8-membered carbocyclic ring;

$R^2$ and $R^6$, taken together with the atoms to which they are attached, form a 4-, 5-, 6-, 7-, 8-, 9-, or 10-membered heterocyclic ring;

$R^4$ and $R^6$, taken together with the atoms to which they are attached, form a 4-, 5-, 6-, 7-, 8-, 9-, or 10-membered heterocyclic ring;

$R^2$ and $R^8$, taken together with the atoms to which they are attached, form a 3-, 4-, 5-, 6-, 7-, or 8-membered carbocyclic ring; or $R^2$ and $R^4$, taken together with the atoms to which they are attached, form a 3-, 4-, 5-, 6-, 7-, or 8-membered carbocyclic ring.

In some cases, when G is —NH2, at least one of $R^1$, $R^2$, $R^3$, and $R^4$ is other than H.

In some cases, $R^5$ and $R^6$ are independently selected from the group consisting of H, methyl, and ethyl. In some cases, $R^5$ and $R^6$, taken together with the nitrogen atom to which they are attached, form a 5-membered heterocyclic ring.

In some cases, wherein $R^4$ is methyl and/or $R^3$ is methyl. In some cases, $R^3$ and $R^4$, taken together with the carbon atom to which they are attached, form a 3-membered carbocyclic ring.

In some cases, $R^2$ is methyl and/or $R^1$ is methyl. In some cases, $R^1$ and $R^2$, taken together with the carbon atom to which they are attached, form a 3-membered carbocyclic ring.

In some cases, G is —$CR^7R^8NR^5R^6$, and $R^2$ and $R^6$, taken together with the atoms to which they are attached, form a 6-membered heterocyclic ring. In some cases, $R^5$ is methyl.

In some cases, G is —$NR^5R^6$, and $R^2$ and $R^6$, taken together with the atoms to which they are attached, form a 4- or 6-membered heterocyclic ring. In some cases, $R^5$ is H.

In some cases, $R^7$ and $R^8$ are both H.

A compound of formula I includes, but is not limited to, the following compounds:

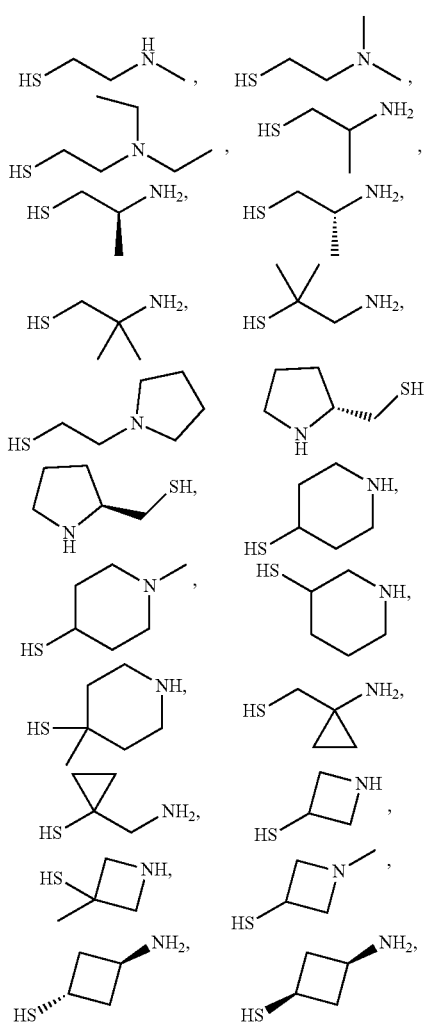

and disulfides thereof.

A compound of formula I includes, but is not limited to, the following compounds:

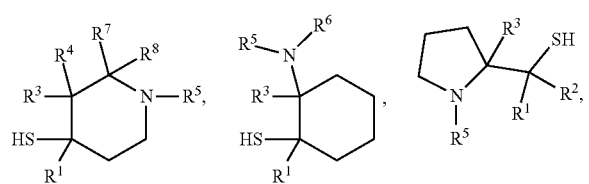

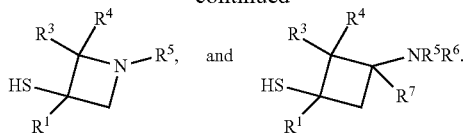

In some cases, $R^1$, $R^2$, $R^3$, $R^4$, $R^5$, $R^6$, $R^7$, and $R^8$ are independently selected from the group consisting of H and $C_{1-5}$alkyl. In some cases, $R^1$, $R^2$, $R^3$, $R^4$, $R^5$, $R^6$, $R^7$, and $R^8$ are independently selected from the group consisting of H and methyl.

Suitable compositions comprise a compound of formula II, formula III, or a disulfide thereof:

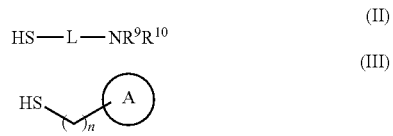

wherein:

L is a hydrocarbon linking group;

$R^9$ and $R^{10}$ are independently selected from the group consisting of H, $C_{1-5}$alkyl, and $CO(C_{1-5}alkyl)$; or $R^9$ and $R^{10}$, taken together with the nitrogen atom to which they are attached, form a 3-, 4-, 5-, 6-, 7-, or 8-membered heterocyclic ring;

A is a heterocyclic ring contain one N atom; and n is 0, 1, 2, or 3.

In some cases, the compound of formula II is not cysteamine.

In some cases, the S atom in the compound of formula II or formula III is a distance of about 3.6 Angstroms to about 4.7 Angstroms from the N atom in the compound, such as about 3.8 Angstroms to about 4.4 Angstroms, about 4.0 Angstroms to about 4.2 Angstroms, or about 4.1 Angstroms from the N atom in the compound.

In some cases, L is a 3-, 4-, 5-, 6-, 7-, or 8-membered cycloalkyl ring or a 6-membered aryl ring. In some cases, L is $C_{1-5}$ alkyl. In some cases, L is substituted with one to four groups selected from halo, $C_{1-5}$ alkyl, $C_{3-5}$ cycloalkyl, and —$CO_2(C_{1-5}alkyl)$.

In some cases, A is a 3-, 4-, 5-, 6-, 7-, or 8-membered monocyclic heterocycloalkyl ring, a 6-, 7-, or 8-membered bicyclic heterocycloalkyl ring, or a 5- or 6-membered heteroaryl ring.

In some cases, the compound of formula III has a structure Ma:

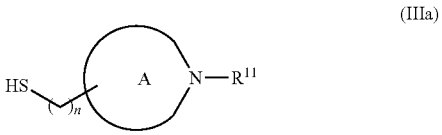

wherein $R^{11}$ is selected from the group consisting of H and $C_{1-5}$ alkyl.

In some cases, A is substituted with one to four groups selected from halo, $C_{1-5}$alkyl, $C_{3-5}$ cycloalkyl, and —$CO_2(C_{1-5}$ alkyl).

In some cases, the compound of formula II, formula III, or disulfide thereof depletes cystine in a subject in an amount that is at least 70% of the level of depletion of cystine by cysteamine.

In various embodiments, the disclosure provides a compound as disclosed herein (e.g., a compound as represented by formula I, formula II, or formula III, or a disulfide thereof), wherein the compound or disulfide thereof produces reduced levels of dimethyl sulfide when administered to a subject compared to the level of dimethyl sulfide produced when cysteamine is administered to a subject. In some cases, least 2-fold less dimethyl sulfide is produced when the compound of formula I, formula II, or formula III, or disulfide thereof is administered to a subject.

In various embodiments, the disclosure provides a compound as disclosed herein (e.g., a compound as represented by formula I, formula II, or formula III, or a disulfide thereof), wherein the compound or disulfide thereof inhibits glutamate-induced excitotoxicity (i.e., provides neuroprotection). In some cases, the compound of formula I, formula II, or formula III, or disulfide thereof demonstrates at least 50% cell survival (expressed as a percent of the cell survival for 100 µM cysteamine), under conditions as described herein.

In various embodiments, the disclosure provides a method of treating a patient suffering from a disease for which treatment with cysteamine is indicated comprising administering to the patient an effective amount of a composition comprising a compound as disclosed herein (e.g., a compound as represented by formula I, formula II, or formula III, or a disulfide thereof), wherein the compound or disulfide thereof is resistant to metabolism by cysteamine dioxygenase (ADO). In some cases, less than 20% of the compound of formula I, formula II, or formula III, or disulfide thereof is metabolized by ADO when assayed by consumption of oxygen using an oxygen sensitive fluorescent probe.

Diseases for which treatment with cysteamine is indicated include, but are not limited to, cystinosis, fatty liver disease, fibrosis, a thrombotic disease, an MECP-2 related disorder, an inherited mitochondrial disease, a neurological disease or disorder, inflammation and cancer.

Fatty liver diseases include, but are not limited to, non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Fibrosis includes, but is not limited to, atherosclerosis, asthma, cardiac fibrosis, organ transplant fibrosis, colloid and hypertrophic scar, muscle fibrosis, pancreatic fibrosis, bone-marrow fibrosis, interstitial liver fibrosis, cirrhosis of liver and gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, renal fibrosis, and chronic kidney disease, cystic fibrosis and Alport's disease.

Thrombotic diseases include, but are not limited to, sickle cell disease, deep vein thrombosis, pulmonary embolism, cardiac embolism, hypercoagulable state, thrombophilia, Factor V Leiden, Antithrombin III deficiency, Protein C deficiency, Protein S deficiency, Prothrombin gene mutation (G20210A), Hyperhomcysteinemia, antiphospholipid antibody syndrome (APS), anticardiolipin antibody (ACLA) thrombosis syndrome, or lupus anticoagulant (LA) syndrome.

Neurological diseases or disorders include, but are not limited to, Huntington's Disease, Parkinson's Disease, amyotrophic lateral sclerosis, multiple sclerosis, Alzheimer's disease spinal muscle atrophy, concussion, stroke, and traumatic brain injury (CTE).

MECP-2 related diseases include, but are not limited to, Rett syndrome, autism, pervasive development disorder, non-syndromic mental retardation, idiopathic neonatal encephalopathy and idiopathic cerebral palsy.

Inherited mitochondrial diseases include, but are not limited to, Friedreich's ataxia, Leber's hereditary optic neuropathy (LHON), myoclonic epilepsy and ragged-red fibers, mitochondrial encephalomyopathy, lactic acidosis, and stroke-like syndrome (MELAS), Kearn-Sayre syndrome and subacute necrotizing encephalopathy (Leigh's Syndrome).

Cancers include, but are not limited to, breast cancer, melanoma, prostate cancer, pancreatic cancer, head and neck cancer, lung cancer, non small-cell lung carcinoma, renal cancer, colorectal cancer, colon cancer, ovarian cancer, liver cancer and gastric cancer.

BRIEF DESCRIPTION OF THE DRAWINGS

FIG. 1 is a graph showing the relationship between the sulfur-nitrogen distance of a compound as disclosed herein compared to its level of cystine depletion.

DETAILED DESCRIPTION

Definitions

As used herein and in the appended claims, the singular forms "a," "an," and "the" include plural referents unless the context clearly dictates otherwise. Thus, for example, reference to "a derivative" includes a plurality of such derivatives and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECH- NOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

As used herein, a "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In some embodiments, such as for fatty liver disease, a therapeutically effective amount of the compound ameliorates one or more symptoms, including but not limited to, liver fibrosis, fat content of liver, incidence of or progression of cirrhosis, incidence of hepatocellular carcinoma, increased hepatic aminotransferase levels, such as ALT and AST, increased serum ferritin, elevated levels of gamma-glutamyltransferase (gamma-GT), and elevated levels of plasma insulin, cholesterol and triglyceride. In some embodiments, such as for a neurodegenerative disease, a therapeutically effective amount of the compound increases the level of brain-derived neurotrophic factor (BDNF). In some embodiments, such as for a neurodegenerative disease, a therapeutically effective amount of the compound inhibits tissue transglutaminase. In some embodiments, such as for a neurodegenerative disease, a therapeutically effective amount of the compound increases heat shock DnaJ-containing protein 1b.

As used herein "a disease for which treatment with cysteamine is indicated" refers to a disease in which increasing the level of cysteamine and/or reducing the level of cystine in a patient is beneficial. Contemplated diseases, include, but are not limited to any of the diseases listed herein, including those in the "Indications, Dosing and Administration" section.

"Treatment" refers to prophylactic treatment or therapeutic treatment. In certain embodiments, "treatment" refers to administration of a compound or composition to a subject for therapeutic or prophylactic purposes.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a therapeutically effective amount of a compound of the disclosure, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

As used herein "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

As used herein, the term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human. In various embodiments, the subject is a child or adolescent.

In one aspect, a method is provided for treating a patient suffering from a disease for which treatment with cysteamine is indicated. The method comprises administering to the patient an effective amount of a composition comprising a compound of formula I or a disulfide thereof:

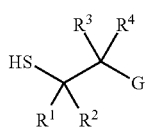
(I)

wherein:

$R^1$ and $R^2$ are independently selected from the group consisting of H and $C_{1-5}$alkyl; or $R^1$ and $R^2$, taken together with the carbon atom to which they are attached, form a 3-, 4-, 5-, 6-, 7-, or 8-membered carbocyclic ring;

$R^3$ and $R^4$ are independently selected from the group consisting of H and $C_{1-5}$alkyl; or $R^3$ and $R^4$, taken together with the carbon atom to which they are attached, form a 3-, 4-, 5-, 6-, 7-, or 8-membered carbocyclic ring;

G is selected from the group consisting of —$NR^5R^6$ and —$CR^7R^8NR^5R^6$;

$R^5$ and $R^6$ are independently selected from the group consisting of H and $C_{1-5}$alkyl; or $R^5$ and $R^6$, taken together with the nitrogen atom to which they are attached, form a 3-, 4-, 5-, 6-, 7-, or 8-membered heterocyclic ring;

$R^7$ and $R^8$ are independently selected from the group consisting of H and $C_{1-5}$alkyl; or $R^7$ and $R^8$, taken together with the carbon atom to which they are attached, form a 3-, 4-, 5-, 6-, 7-, or 8-membered carbocyclic ring;

$R^2$ and $R^6$, taken together with the atoms to which they are attached, form a 4-, 5-, 6-, 7-, 8-, 9-, or 10-membered heterocyclic ring;

$R^4$ and $R^6$, taken together with the atoms to which they are attached, form a 4-, 5-, 6-, 7-, 8-, 9-, or 10-membered heterocyclic ring;

$R^2$ and $R^8$, taken together with the atoms to which they are attached, form a 3-, 4-, 5-, 6-, 7-, or 8-membered carbocyclic ring; or $R^2$ and $R^4$, taken together with the atoms to which they are attached, form a 3-, 4-, 5-, 6-, 7-, or 8-membered carbocyclic ring.

In some cases, when G is —NH2, at least one of $R^1$, $R^2$, $R^3$, and $R^4$ is other than H.

In some cases, $R^5$ and $R^6$ are independently selected from the group consisting of H, methyl, and ethyl. In some cases, $R^5$ and $R^6$, taken together with the nitrogen atom to which they are attached, form a 5-membered heterocyclic ring.

In some cases, wherein $R^4$ is methyl and/or $R^3$ is methyl. In some cases, $R^3$ and $R^4$, taken together with the carbon atom to which they are attached, form a 3-membered carbocyclic ring.

In some cases, $R^2$ is methyl and/or $R^1$ is methyl. In some cases, $R^1$ and $R^2$, taken together with the carbon atom to which they are attached, form a 3-membered carbocyclic ring.

In some cases, G is —$CR^7R^8NR^5R^6$, and $R^2$ and $R^6$, taken together with the atoms to which they are attached, form a 6-membered heterocyclic ring. In some cases, $R^5$ is methyl.

In some cases, G is —$NR^5R^6$, and $R^2$ and $R^6$, taken together with the atoms to which they are attached, form a 4- or 6-membered heterocyclic ring. In some cases, $R^5$ is H.

In some cases, $R^7$ and $R^8$ are both H.

A compound of formula I includes, but is not limited to, the following compounds:

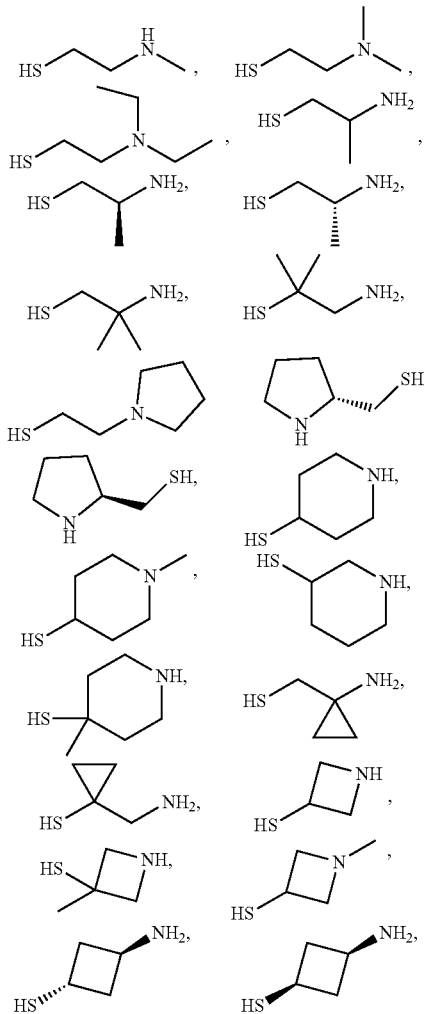

and disulfides thereof.

A compound of formula I includes, but is not limited to, the following compounds:

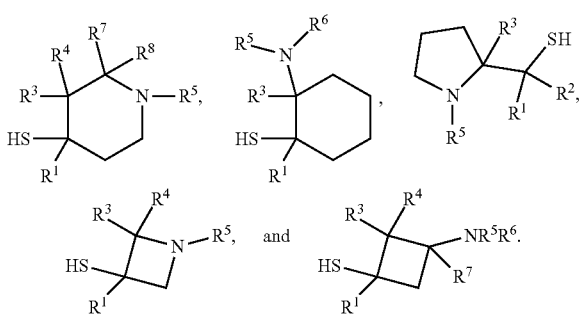

In some cases, $R^1$, $R^2$, $R^3$, $R^4$, $R^5$, $R^6$, $R^7$, and $R^8$ are independently selected from the group consisting of H and $C_{1-5}$ alkyl. In some cases, $R^1$, $R^2$, $R^3$, $R^4$, $R^5$, $R^6$, $R^7$, and $R^8$ are independently selected from the group consisting of H and methyl.

In one aspect, a method is provided for treating a patient suffering from a disease for which treatment with cysteamine is indicated. The method comprises administering to the patient an effective amount of a composition comprising a compound of formula II, formula III, or a disulfide thereof:

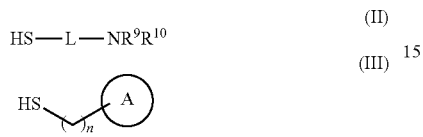

wherein:

L is a hydrocarbon linking group;

$R^9$ and $R^{10}$ are independently selected from the group consisting of H, $C_{1-5}$ alkyl, and $CO(C_{1-5}alkyl)$; or $R^9$ and $R^{10}$, taken together with the nitrogen atom to which they are attached, form a 3-, 4-, 5-, 6-, 7-, or 8-membered heterocyclic ring;

A is a heterocyclic ring contain one N atom; and n is 0, 1, 2, or 3.

In some cases, the compound of formula II is not cysteamine.

In some cases, the S atom in the compound of formula II or formula III is a distance of about 3.6 Angstroms to about 4.7 Angstroms from the N atom in the compound, such as about 3.8 Angstroms to about 4.4 Angstroms, about 4.0 Angstroms to about 4.2 Angstroms, or about 4.1 Angstroms from the N atom in the compound.

In some cases, L is a 3-, 4-, 5-, 6-, 7-, or 8-membered cycloalkyl ring or a 6-membered aryl ring. In some cases, L is $C_{1-5}$ alkyl. In some cases, L is substituted with one to four groups selected from halo, $C_{1-5}$ alkyl, $C_{3-5}$ cycloalkyl, and —$CO_2(C_{1-5}alkyl)$.

In some cases, A is a 3-, 4-, 5-, 6-, 7-, or 8-membered monocyclic heterocycloalkyl ring, a 6-, 7-, or 8-membered bicyclic heterocycloalkyl ring, or a 5- or 6-membered heteroaryl ring.

In some cases, the compound of formula III has a structure Ma:

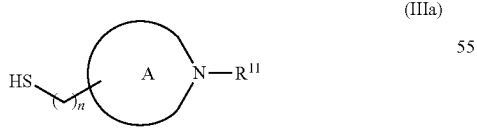

wherein $R^{11}$ is selected from the group consisting of H and $C_{1-5}$ alkyl.

In some cases, A is substituted with one to four groups selected from halo, $C_{1-5}$alkyl, $C_{3-5}$ cycloalkyl, and —$CO_2(C_{1-5}$ alkyl).

Compounds disclosed herein also include, but are not limited to,

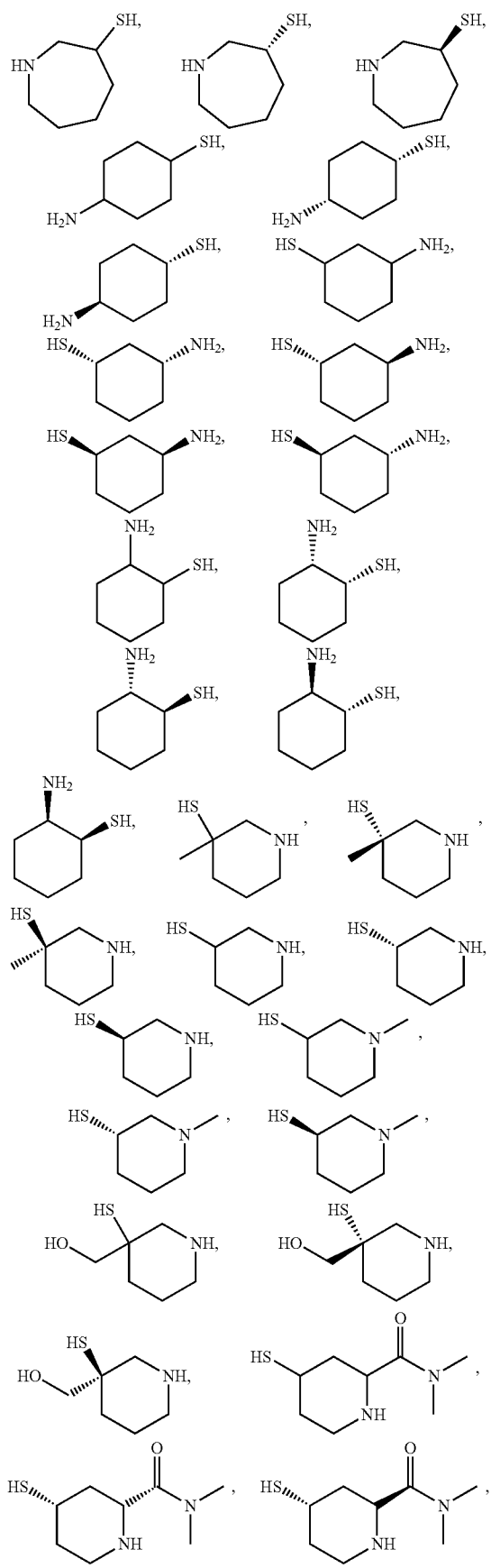

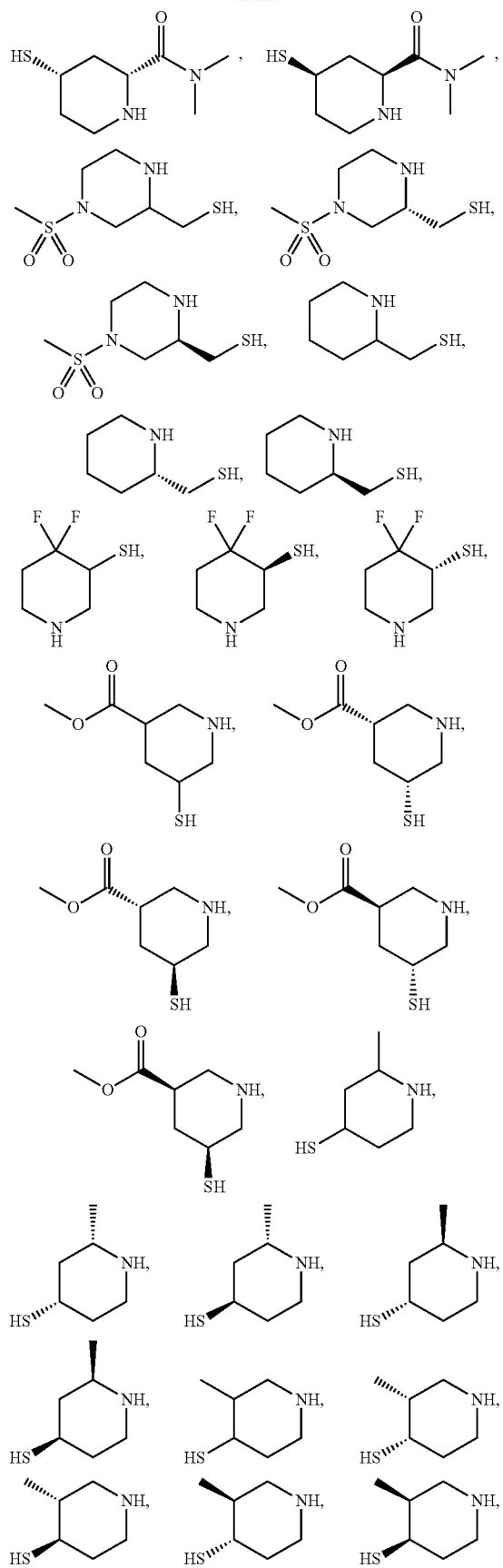
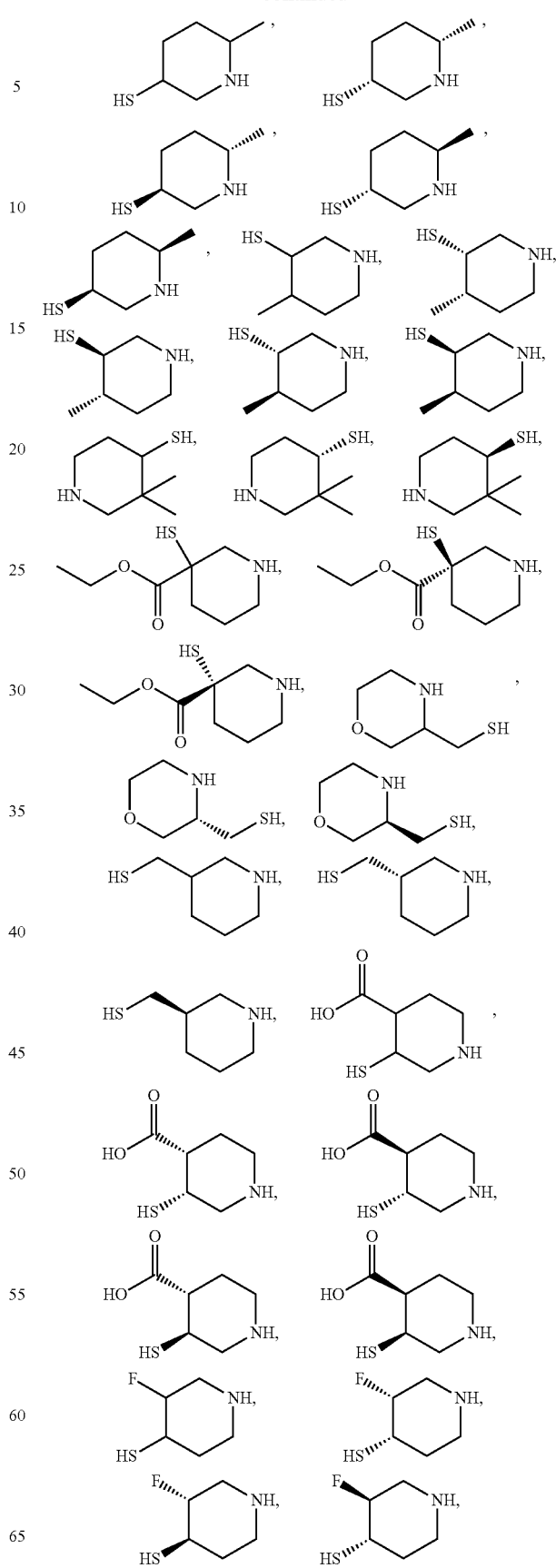

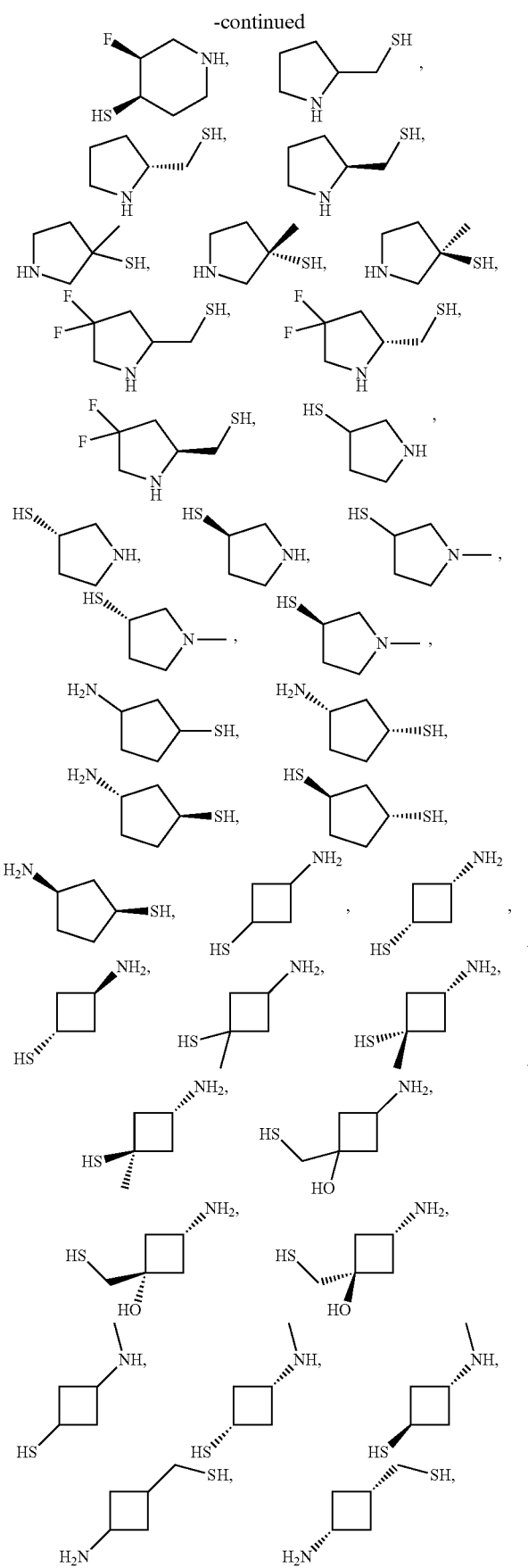
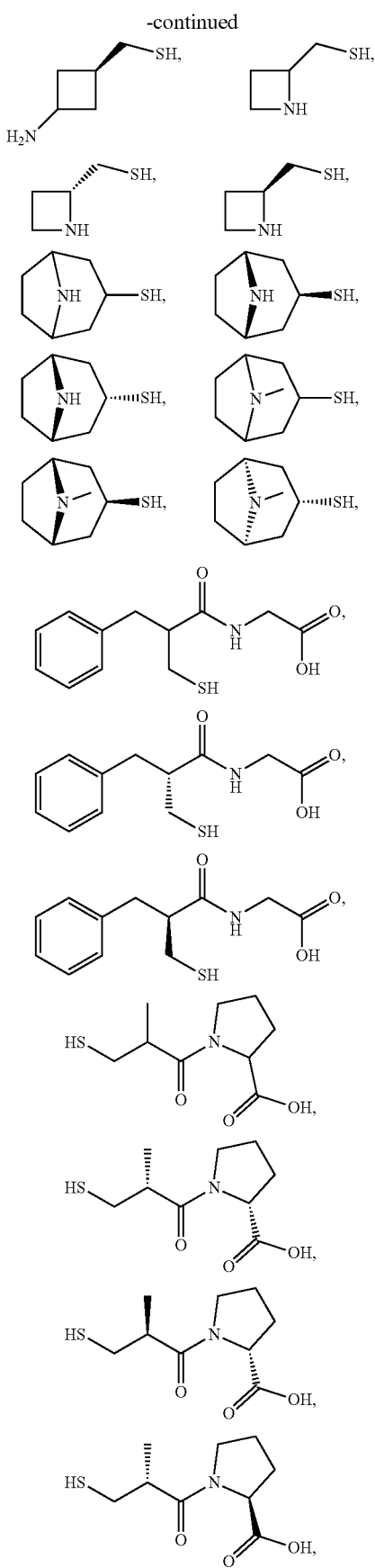

-continued

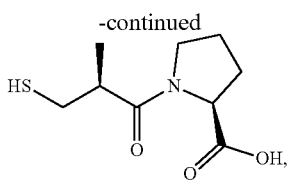

the compounds listed in the tables herein, and disulfides thereof.

Compounds disclosed herein include compounds having the following structure or a disulfide thereof:

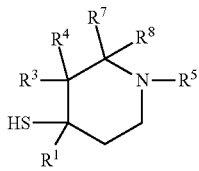

wherein $R^1$ is $C_{1-5}$alkyl; and $R^3$, $R^4$, $R^5$, $R^7$, and $R^8$ are independently selected from the group consisting of H and $C_{1-5}$alkyl.

Compounds disclosed herein include compounds having the following structure or a disulfide thereof:

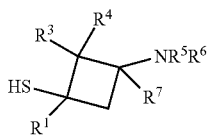

wherein $R^1$, $R^3$, $R^4$, $R^5$, $R^6$, and $R^7$ are independently selected from the group consisting of H and $C_{1-5}$ alkyl.

ADO-Resistant Cysteamine Analogs

The disclosure provides ADO-resistant cysteamine analogs for use in the methods described herein. An "ADO-resistant cysteamine analog" in the present disclosure refers generally to compounds of formula I, formula II, formula III, or a disulfide thereof. ADO-resistant cysteamine analogs generally demonstrate three properties: (1) the compounds are resistant to metabolism by ADO, (2) the compounds cleave cystine in vivo, and (3) the compounds clear stored cystine in patient cystinotic fibroblasts.

As used herein a compound that is "resistant to metabolism by cysteamine dioxygenase" or "resistant to metabolism by ADO" refers to a compound that undergoes less than 50% degradation, for example, less than 40%, less than 30%, less than 25%, less than 20%, less than 15%, less than 10%, less than 8%, less than 7%, less than 6%, less than 5%, less than 4%, less than 3%, less than 2%, less than 1.5%, and/or less than 1% degradation when assayed in the presence of ADO under conditions as described herein. Due to the rapid metabolism and clearance of cysteamine from the body due to ADO, the sustained concentrations of cysteamine necessary for therapeutic effect are difficult to maintain. Advantageously, compounds that are resistant to metabolism by ADO are more readily maintained at necessary concentrations for therapeutic effect.

A compound that cleaves cystine in vivo refers to a compound that converts cystine to cysteine and a mixed disulfide containing cysteine and the compound. Such compounds typically have a reactivity similar to or greater than the reactivity of cysteamine for cystine, such as at least at least 50%, at least 75%, at least 90%, at least 100%, at least 110%, at least 120%, at least 130%, at least 140%, at least 150%, at least 160%, at least 170%, at least 180%, at least 190%, and/or at least 200% of the reactivity of cysteamine for cystine, as determined under conditions as described herein.

A compound that clears stored cystine in patient cystinotic fibroblasts refers to a compound that facilitates transport of cystine out of lysosomes. Such compounds typically deplete cystine in an amount similar to or greater than the depletion of cystine by cysteamine, such as at least 25%, at least 40%, at least 50%, at least 60%, at least 70%, at least 75%, at least 80%, at least 85%, at least 90%, at least 95%, at least 100%, at least 105%, and/or at least 110% of the depletion by cysteamine, as determined under conditions as described herein.

The ADO-resistant cysteamine analogs also include biologically active metabolites or derivatives thereof, and includes salts, esters, amides, alkylate compounds, prodrugs, analogs, phosphorylated compounds, sulfated compounds, or other chemically modified forms thereof (e.g., chemically modified forms prepared by labeling with radionucleotides or enzymes and chemically modified forms prepared by attachment of polymers such as polyethylene glycol). Thus, the compounds of formula I, formula II, or formula III can be administered in the form of a pharmacologically acceptable salt, ester, amide, prodrug or analog or as a combination thereof.

Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Dimethyl Sulfide (DMS) Production

Compounds that produce reduced levels of dimethyl sulfide when administered to a subject (compared to the level produced when cysteamine is administered) are desirable because unpleasant side effects associated with cysteamine (e.g., halitosis) may be reduced. A compound that produces reduced levels of dimethyl sulfide when administered to a subject generally produces at least 2-fold less dimethyl sulfide, such as at least 3-fold less, 4-fold less, 5-fold less, 6-fold less, 8-fold less, 10-fold less, 15-fold less, and/or 20-fold less dimethyl sulfide, compared to the level of dimethyl sulfide produced when cysteamine is administered to the subject at the same dose and same time after administration under conditions as described herein. For example, the level of dimethyl sulfide can be measured by administering the compound in a dose of about 10 mg/kg to about 500 mg/kg, such as about 25 mg/kg to about 400 mg/kg, about 50 mg/kg to about 300 mg/kg, about 75 mg/kg to about 200 mg/kg, about 10 mg/kg, about 25 mg/kg, about 50 mg/kg, about 75 mg/kg, about 100 mg/kg, about 150 mg/kg, about 200 mg/kg, about 300 mg/kg, about 400 mg/kg, and/or about 500 mg/kg, and by measuring the dimethyl sulfide level about 10 minutes to 4 hours after administration, such as about 15 minutes to about 2 hours, about 30 minutes to about 1 hour, about 15 minutes, about 30 minutes, about 1 hour, and/or about 2 hours after administration.

Neuroprotection

Excitotoxicity disorders affect the central nervous and peripheral nervous systems and can lead to progressive neurodegeneration. Excitotoxicity results from excess glutamate being secreted by various cells, including immune cells and neurons, in the brain. Glutamate is the primary excitatory neurotransmitter in the mammalian nervous system. Prolonged glutamate signaling leads to a type of toxicity characterized by elevated mitochondrial activity, gradual glutathione (GSH) depletion, oxidative stress and apoptosis (Shih et al., J Neurosci. 26:10514-523, 2006). Cysteamine is capable of inhibiting glutamate-induced excitotoxicity in St-HdhQ$^{111/111}$ cells. A compound that inhibits glutamate-induced excitotoxicity (i.e., provides neuroprotection) generally provides at least 50% cell survival (expressed as a percent of the cell survival for 100 µM cysteamine), such as at least 65%, at least 75%, at least 80%, at least 90%, and/or at least 95% cell survival, under conditions as described herein.

Pharmaceutical Formulations

The disclosure provides compounds useful in the treatment of diseases in which therapy with cysteamine is indicated. To administer compounds of the disclosure to patients or test animals, it is preferable to formulate the compounds in a composition comprising one or more pharmaceutically acceptable carriers. Pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The compounds may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Pharmaceutical compositions of the disclosure containing a compound as disclosed herein as an active ingredient may contain pharmaceutically acceptable carriers or additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the disclosure.

Formulation of the pharmaceutical composition will vary according to the route of administration selected (e.g., solution, emulsion). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, the compounds of this disclosure can be lyophilized for storage and reconstituted in a suitable carrier prior to use. Any suitable lyophilization and reconstitution techniques can be employed. It is appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the disclosure provides use of an enterically coated composition. Enteric coatings prolong release until the active agent reaches the intestinal tract, typically the small intestine. Because of the enteric coatings, delivery to the small intestine is improved thereby improving uptake of the active ingredient while reducing gastric side effects. Exemplary enterically coated products are described in International Publication No. WO 2007/089670 published Aug. 9, 2007, which is incorporated in its entirety herein.

In some embodiments, the coating material is selected such that the therapeutically active agent is released when the dosage form reaches the small intestine or a region in which the pH is greater than pH 4.5. The coating may be a pH-sensitive materials, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5 or between about 5.5 to 6.5. For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine. In order to provide predictable dissolution corresponding to the small intestine transit time of about 3 hours (e.g., 2-3 hours) and permit reproducible release therein, the coating should begin to dissolve at the pH range within the small intestine. Therefore, the amount of enteric polymer coating should be sufficient to substantially dissolve during the approximate three hour transit time within the small intestine, such as the proximal and mid-intestine.

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See, Remington's at page 1590, and Zeitova et al. (U.S. Pat. No. 4,432,966), for descriptions of suitable enteric coating compositions. Accordingly, increased adsorption in the small intestine due to enteric coatings of product compositions can result in improved efficacy.

Generally, the enteric coating comprises a polymeric material that prevents product release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a pKa in the range of about 3 to 5. Suitable enteric coating materials include, but are not limited to, polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS). In one embodiment, the product composition is administered in oral delivery vehicle, including but not limited to, tablet or capsule form. Tablets are manufactured by first enterically coating the product. A method for forming tablets herein is by direct compression of the powders containing the enterically coated product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In a further embodiment, the product is formulated as a capsule. In one embodiment, the capsule comprises the product and the capsule is then enterically coated. Capsule formulations are prepared using techniques known in the art.

The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an insoluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For further detail, see the Handbook of Pharmaceutical Controlled Release Technology, Wise, ed., Marcel Dekker, Inc., New York, N.Y. (2000), incorporated by reference herein in its entirety, e.g. Chapter 22 ("An Overview of Controlled Release Systems").

The concentration of product in these formulations can vary widely, for example from less than about 0.5%, usually at or at least about 1% to as much as 15 or 20% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

Compositions useful for administration may be formulated with uptake or absorption enhancers to increase their efficacy. Such enhancers include, for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

The enterically coated product can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the cysteamine product. Oral delivery vehicles contemplated for use herein include tablets or capsules. For solid compositions, diluents are typically necessary to increase the bulk of a tablet or capsule so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a oral delivery vehicle formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, hypromellose, and the like), and Veegum. Lubricants are used to facilitate oral delivery vehicle manufacture; examples of suitable lubricants include, for example, magnesium stearate, calcium stearate, and stearic acid, and are typically present at no more than approximately 1 weight percent relative to tablet weight. Disintegrants are used to facilitate oral delivery vehicle, (e.g., a tablet) disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of cysteamine product to the stabilizing agent is at least about 1:500 w/w, more commonly about 1:99 w/w.

The tablet, capsule or other oral delivery system is manufactured by first enterically coating the product. A method for forming tablets herein is by direct compression of the powders containing the enterically coated cysteamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In an alternative embodiment, the enterically coated product is granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein.

For administration of the dosage form, i.e., the tablet or capsule comprising the enterically coated product, a total weight in the range of approximately 100 mg to 1000 mg is used. The dosage form is orally administered to a patient suffering from a condition for which treatment with cysteamine would typically be indicated.

Indications, Dosing and Administration

The disclosure provides methods of treating a patient (e.g., a human patient) suffering from a disease where therapy with cysteamine is indicated, comprising administering to the patient a therapeutically effective amount of a compound as disclosed herein.

In some embodiments of the methods, the disease is cystinosis. In some embodiments the disease is nephropathic cystinosis. In some embodiments of the methods, the disease is a fatty liver disease. In some embodiments, the fatty liver disease is non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy or other fatty liver disease. The term "fatty liver disease" may include or exclude NASH. In some embodiments of the methods, the disease is a fibrosis. In some embodiments, the fibrosis is atherosclerosis, asthma, cardiac fibrosis, organ transplant fibrosis, colloid and hypertrophic scar, muscle fibrosis, pancreatic fibrosis, bone-marrow fibrosis, interstitial liver fibrosis, cirrhosis of liver and gallbladder, scleroderma, pulmonary fibrosis, diffuse parenchymal lung disease, idiopathic interstitial fibrosis, interstitial pneumonitis, desquamative interstitial pneumonia, respiratory bronchiolitis, interstitial lung disease, acute interstitial pneumonitis, nonspecific interstitial pneumonia, cryptogenic organizing pneumonia, lymphocytic interstitial pneumonia, renal fibrosis, chronic kidney disease, cystic fibrosis, or Alport's disease. In some embodiments of the methods, the disease is a thrombotic disease. In some embodiments, the thrombotic disease is sickle cell disease, deep vein thrombosis, pulmonary embolism, cardiac embolism, hypercoagulable state, thrombophilia, Factor V Leiden, Antithrombin III deficiency, Protein C deficiency, Protein S deficiency, Prothrombin gene mutation (G20210A), Hyperhomcysteinemia, antiphospholipid antibody syndrome (APS), anticardiolipin antibody (ACLA) thrombosis syndrome, or lupus anticoagulant (LA) syndrome. In some embodiments of the methods, the disease is an MECP-2 related disorder such as Rett syndrome, autism, pervasive development disorder, non-syndromic mental retardation, idiopathic neonatal encephalopathy or idiopathic cerebral palsy. In some embodiments of the methods, the disease is an inherited mitochondrial disease such as Friedreich's ataxia, Leber's hereditary optic neuropathy (LHON), myoclonic epilepsy and ragged-red fibers, mitochondrial encephalomyopathy, lactic acidosis, and stroke-like syndrome (MELAS), Kearn-Sayre syndrome or subacute necrotizing encephalopathy (Leigh's Syndrome). In some embodiments of the methods, the disease is a neurological disease or disorder such as Huntington's Disease, Parkinson's Disease, amyotrophic lateral sclerosis, multiple sclerosis, Alzheimer's disease spinal muscle atrophy, concussion, stroke, or traumatic brain injury (CTE). In some embodiments of the methods, the disease is inflammation. In some embodiments of the methods, the disease is cancer, for example, breast cancer, melanoma, prostate cancer, pancreatic cancer, head and neck cancer, lung cancer, non small-cell lung carcinoma, renal cancer, colorectal cancer, colon cancer, ovarian cancer, liver cancer or gastric cancer.

As used herein, "renal fibrosis or chronic kidney disease" refers to a progressive disorder of the kidney characterized by excessive deposit(s) of extracellular matrix (ECM) and resulting in glomerular sclerosis and renal tubule-interstitium fibrosis. Excessive deposit of fibrous tissue replaces healthy kidney tissue, damaging kidney structure and impairing kidney function. Exemplary renal fibrosis or chronic kidney disease include, but are not limited to, chronic renal insufficiency (CRI), stage III, IV or V chronic kidney disease, nephropathy, glomerulosclerosis, glomerulonephritis, diabetes, fibrocystic kidney disease, fibrotic kidney cancer, or renal interstitial fibrosis.

The compound is administered in a therapeutically effective amount. The amount of compound to be administered is dependent on the age, weight, and general condition of the patient, the severity of the condition being treated, and the judgment of the prescribing-physician. Suitable therapeutic amounts are determined by standard methods by those skilled in the art. In some embodiments, the dose is administered either one or two times per day. In some embodiments, the dose is administered multiple times per day. In some embodiments, an effective dosage of compound is within the range of about 0.01 mg to about 1000 mg per kg (mg/kg) of body weight per day. Further, the effective dose may be about: 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. In some embodiments, the administration route is oral. In some embodiments, the administration route is transdermal.

The compound is administered in a therapeutically effective amount; typically, the composition is in unit dosage form. The amount of compound administered is, of course, dependent on the age, weight, and general condition of the patient, the severity of the condition being treated, and the judgment of the prescribing physician. Suitable therapeutic amounts will be known to those skilled in the art and/or are described in the pertinent reference texts and literature. In one aspect, the dose is administered either one time per day or multiple times per day. The product may be administered one, two or three or four times per day. In some embodiments, an effective dosage of product may be within the range of 0.01 mg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the dose above may be the total daily dose, or may be the dose administered in one of the one, two or three daily administrations. In some embodiments, the product is administered at a total daily dose of from approximately 0.25 $g/m^2$ to 4.0 $g/m^2$ body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 $g/m^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 $g/m^2$ or may range between any two of the foregoing values. In some embodiments, the product may be administered at a total daily dose of about 0.5-2.0 $g/m^2$ body surface area, or 1-1.5 $g/m^2$ body surface area, or 0.5-1 $g/m^2$ body surface area, or about 0.7-0.8 $g/m^2$ body surface area, or about 1.35 $g/m^2$ body surface area, or about 1.3 to about 1.95 grams/m2/day, or about 0.5 to about 1.5 grams/m2/day, or about 0.5 to about 1.0 grams/m2/day, preferably at a frequency of fewer than four times per day, e.g. three, two or one times per day. Salts or esters of the same active ingredient may vary in molecular weight depending on the type and weight of the salt or ester moiety. For administration of the dosage form, e.g., a tablet or capsule or other oral dosage form comprising the enterically coated product, a total weight in the range of approximately 100 mg to 1000 mg is used. In certain embodiments, the amount of active ingredient in a tablet or capsule is approximately 15, 20, 25, 50, 75, 100, 125, 150, 175, 200, 250, 300, 400 or 500 mg. Administration may continue for at least 3 months, 6 months, 9 months, 1 year, 2 years, or more.

The compositions of the invention can be used in combination with other drugs or therapies for each indication contemplated herein. Combinations with other drugs or therapies that are part of the standard of care for each indication are specifically contemplated herein.

The compounds and other drugs/therapies can be administered in combination either simultaneously in a single composition or in separate compositions. Alternatively, the administration is sequential. In some embodiments, the patient is pre-dosed with the compound before the administration of the other drug/therapy.

The effectiveness of a method or composition of the described herein can be assessed, for example, by measuring leukocyte cystine concentrations in subjects affected by cystinosis. Additional measures of the efficacy of the methods of the disclosure include assessing relief of symptoms associated with fatty liver disease including, but not limited to, liver fibrosis, fat content of liver, incidence of or progression of cirrhosis, incidence of hepatocellular carcinoma, elevated hepatic aminotransferase levels, increased alanine aminotransferase (ALT), increased aspartate aminotransferase (AST), and elevated serum ferritin. Dosage adjustment and therapy can be made by a medical specialist depending upon, for example, the severity of fatty liver disease and/or the concentration of cystine. For example, treatment of fatty liver disease may result in a reduction in hepatic transaminase of between approximately 10% to 40% compared to levels before treatment. In a related embodiment, treatment results in a reduction in alanine aminotransferase levels in a treated patient to approximately 30%, 20% or 10% above normal ALT levels, or at normal ALT levels (≥40 iu/L). In another embodiment, treatment with cysteamine product results in a reduction in aspartate aminotransferase levels in a patient to approximately 30%, 20% or 10% above normal AST levels or back to normal AST levels.

The methods of the invention also include use of a compound as disclosed herein in preparation of a medicament for treatment of a disease in which administration of cysteamine is indicated, and use of a compound as disclosed herein in preparation of a medicament for administration in combination with another agent for treating a disease where administration of cysteamine is indicated. Further provided are kits comprising a compound as disclosed herein for treatment of a disease in which administration of cysteamine is indicated, optionally another agent for treatment, and instructions for use in treatment of a disease where administration of cysteamine is indicated.

Animal Models

The compounds disclosed herein can be evaluated in animal models known in the art for the disease indications contemplated herein.

For example, a number of mouse models which exhibit steatosis/steatohepatitis exist and include genetically altered leptin-deficient (ob/ob) or leptin resistant (db/db) and the dietary methionine/choline deficient (MCD) model. Studies comparing male and female rats of varying strains (Wistar, Sprague-Dawley, Long-Evans) with a mouse strain (C57BL/6) as models for NASH can be carried out. More recently the use of supra-nutritional diets in animals has resulted in a NAFLD model that physiologically more resembles the human phenotype. The medical conditions most commonly associated with NAFLD are obesity, Type II diabetes and dyslipidemia. These conditions can be induced by feeding mice and rats with high fat or sucrose diets. Rats fed with a >70% fat-rich diet for 3 weeks develop pan-lobular steatosis, patchy inflammation, enhanced oxidative stress, and increased plasma insulin concentrations suggesting insulin resistance. NASH mice have been induced through intragastric overfeeding. Mice were fed up to 85% in excess of their standard intake for 9 weeks. The mice became obese with 71% increase in final body weight; they demonstrated increase white adipose tissue, hyperglycemia, hyperinsulinemia, hyperleptinemia, glucose intolerance and insulin resistance. Of these mice 46% developed increased ALT (121=1-27 vs 13+/−1 U/L) as well as histologic features suggestive of NASH. The livers of the overfed mice were about twice as large expected, beige in color with microscopic evidence of lipid droplets, cytoplasmic vacuoles and clusters of inflammation.

Mouse models of NASH are created through specific diets (methionine choline deficient, MCD) or intragastric overfeeding. These mice develop serologic and histologic features of NASH. NASH mice are useful in screening and measuring the effects the compounds disclosed herein on NASH related disease and disorders.

Animal models for kidney fibrosis are known in the art and described, for example, in Eddy et al., "Investigating mechanisms of chronic kidney disease in mouse models" Pediatr Nephrol. 2011 Jun. 22.

Animal models of Huntington's Disease and Parkinson's disease are described in the art and useful to determine the effects of the compounds disclosed herein in subjects suffering from disease. See, e.g., Karpuj et al., "Evidence for a role for transglutaminase in Huntington's disease and the potential therapeutic implications." Neurochem Int. (2002) January; 40(1):31-6, and Bove et al., "Neurotoxin-based models of Parkinson's disease." Neuroscience. 2011, Nov. 10.

Additional animal models for other indications are available in the art and are useful to measure the efficacy of the compounds disclosed herein in said disorders.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

EXAMPLES

General Methods

Cystine Reactivity Assay

Cystine reactivity was assessed by incubating 3 mM test compound with 100 nM BODIPY® FL L-Cystine (Life Tech.) at 30° C., pH 7.4 in phosphate buffer. The initial rate of fluorescence (excitation λ485 nm and emission λ535 nm) increase was used as a measure of cystine reactivity and hence cysteine formation. Compound cystine reactivity was expressed as a percentage of that of 3 mM cysteamine.

Under resting conditions, the inherent fluorescence of BODIPY® FL L-cystine was very low due to the spatial proximity of the two BODIPY molecules causing quenching. Under chemical reaction (disruption of the S—S bond), the spatial distance was increased, the quenching lost, and measured fluorescence increased. Time (minutes) vs. fluorescence (relative fluorescence units—RFU) was plotted and linear regression analysis was performed to generate a slope value corresponding to the reaction rate in RFU/min and an $R^2$ value.

ADO Metabolism Assay

The rate of ADO metabolism was determined by incubating 15 mM test compound with 60 µg/ml human recombinant ADO and 20 nM MitoXpress® 02-sensitive fluorescent probe (Luxcel) at 37° C. in assay buffer/salt in a sealed assay chamber. The initial rate of fluorescence (excitation λ380 nm and emission λ650 nm) increase was used to measure ADO-dependent oxygen depletion activity. The ability of ADO to metabolize compounds and concomitantly consume oxygen was expressed relative to that of 15 mM cysteamine.

Cystine Depletion Assay

The ability of test compounds to deplete cystine from cystinotic human fibroblasts (Coriell) was determined by incubating compounds with cells for 60 min at 37° C., 95% (v/v) air/5% (v/v) $CO_2$ in Minimal Essential Media Eagle. Treated cell samples were subsequently harvested, then homogenized to ensure plasma and lysosomal membrane disruption. Protein was removed by acid precipitation and cystine in the supernatant measured using LC-MS/MS and HILIC chromatography. Protein levels were determined and cystine levels reported as nM per mg/ml protein. Cystine levels after test compound treatment were expressed as a percentage of that of untreated control cells.

Rat Hepatocyte Assay

Rat hepatocytes were used to model in vivo hepatic clearance of the compounds by the ADO enzyme. Briefly, a Hepatocyte Stability Assay was carried out using cryopreserved rat hepatocytes. The test compound was added to cells (e.g., $10^6$ cells) at a concentration of approximately 3 µM (50 µL of 10 mM solution). Other concentrations can also be used. Presence of compound was measured at varying timepoints (0, 5, 15, 30, 45, 60, 90, 120 minutes) by LC-MS/MS analysis and intrinsic clearance ($CL_{int}$) rate was measured. See, e.g., Lubberstedt et al., HepaRG human hepatic cell line utility as a surrogate for primary human hepatocytes in drug metabolism assessment in vitro, J Pharmacol Toxicol Methods 63:59-68, 2010; or Zanelli et al., Comparison of cryopreserved HepaRG cells with cryopreserved human hepatocytes for prediction of clearance for 26 drugs, Drug Metab Dispos 40:104-110, 2012.

Rodent Pharmacokinetic Assays

Pharmacokinetic parameters of a test compound in a rodent species (mouse and/or rat) were determined by administering a test compound at 2 and 10 mg free base equivalents per kg via the intravenous and oral gavage route to groups of three animals per route.

Blood samples were taken at various times after administration, plasma prepared, and submitted to analysis for parent drug using a qualified LC-MS-MS assay. Pharmacokinetics parameters derived from the plasma analytical data were determined using non-compartmental analysis.

Example 1

Activity of N-Substituted Compounds

Compounds were assayed at a concentration of 50 µM or 100 µM according to the general methods described above.

TABLE 1

| Compound | Cysteamine | 1a | 1b | 1c |
|---|---|---|---|---|
| Structure | HS-CH₂CH₂-NH₂ | HS-CH₂CH₂-NH-CH₂CH₃ | HS-CH₂CH₂-N(CH₃)-CH₂CH₃ | HS-CH₂CH₂-N(CH₂CH₃)₂ |
| Cystine Reactivity | 6543 | — | 7933 | 11027 |
| ADO metabolism | 111% | 4% | 9% | 2% |
| Cystine depletion | 101% (106%) | 85% (94%) | 104% (104%) | 98% |
| Rat Hepatocytes $CL_{int}$ (ml/min/mg) | 33.7 | — | 27.0 | 26.3 |
| Rat PK -Half life Bioavailability | 0.5 h 62% | — | 0.3 h 15% | 0.3 h 28% |
| Mouse PK -Half life Bioavailability | 2.4 h 33% | — | — | — |

( ) = disulfide efficacy

As shown in Table 1, compounds 1b and 1c demonstrate increased reactivity with cystine compared to cysteamine, along with similar cystine depletion levels. Compound 1a demonstrates slightly decreased cystine depletion levels as compared to the cystine depletion levels for cysteamine. Advantageously, compounds 1a, 1b, and 1c demonstrate significantly reduced metabolism by ADO compared to cysteamine.

Example 2

Activity of Cyclic N-Substituted Compounds

Compounds were assayed at a concentration of 50 µM or 100 µM according to the general methods described above.

TABLE 2

| Compound | Cysteamine | 2a | 2b | 2c | 2d |
|---|---|---|---|---|---|
| Structure | HS–CH₂CH₂–NH₂ | azetidine-3-thiol | 2-(pyrrolidin-1-yl)ethanethiol | piperidine-4-thiol | 1-methylpiperidine-4-thiol |
| Cystine Reactivity | 6543 | — | 12392 | — | 7332 |
| ADO metabolism | 111% | 7% | 4% | 2% | 1% |
| Cystine depletion | 101% (106%) | 82% | 99% | 73% | 79% |
| Rat Hepatocytes CL$_{int}$ (ml/min/mg) | 33.7 | — | 15.7 | — | 12.6 |
| Rat PK -Half life Bio-availability | 0.5 h 62% | — | — | — | 2.3 h 34% |
| Mouse PK -Half life Bio-availability | 2.4 h 33% | — | 0.4 h 33% | 7.1 h 74% | 3.9 h 38% |

( ) = disulfide efficacy

As shown in Table 2, compounds 2b and 2d demonstrate increased reactivity with cystine compared to cysteamine. The compounds also demonstrates similar (compound 2b) or slightly decreased (compounds 2a, 2c, 2d) cystine depletion levels as compared to the cystine depletion levels for cysteamine. Advantageously, compounds 2a, 2b, 2c, and 2d demonstrate significantly reduced metabolism by ADO compared to cysteamine.

Example 3

Activity of Alkyl Chain-Substituted Compounds

Compounds were assayed at a concentration of 50 µM or 100 µM according to the general methods described above.

3c) or slightly decreased (compounds 3a, 3d) cystine depletion levels as compared to the cystine depletion levels for cysteamine. Advantageously, compounds 3a, 3c, and 3d demonstrate significantly reduced metabolism by ADO compared to cysteamine.

Example 4

Sulfur-Nitrogen Distances and Activity of Compounds

The sulfur-nitrogen distances for each of the compounds in Table 4 were calculated using quantum mechanic calculations according to the following procedure. First, the 2D chemical structures were read into Spartan '14 and auto-

TABLE 3

| Compound | Cysteamine | 3a | 3b | 3c | 3d |
|---|---|---|---|---|---|
| Structure | HS–CH₂CH₂–NH₂ | 3-mercapto-2,2-dimethylpropan-1-amine | 2-mercapto-2-methylpropan-1-amine | 1-mercapto-2-methylpropan-2-amine | (1-(mercaptomethyl)cyclopropyl)methanamine |
| Cystine Reactivity | 6543 | 2284 | — | 7733 | — |
| ADO metabolism | 111% | 14% | — | 9% | 14% |
| Cystine depletion | 101% (106%) | 32% | 97% | 97% | 55% |
| Rat Hepatocytes CL$_{int}$ (ml/min/mg) | 33.7 | — | — | 29.5 | — |
| Rat PK -Half life Bio-availability | 0.5 h 62% | — | — | 0.8 h 23% | — |
| Mouse PK -Half life Bio-availability | 2.4 h 33% | — | — | — | — |

( ) = disulfide efficacy

As shown in Table 3, compound 3c demonstrates increased reactivity with cystine compared to cysteamine. The compounds also demonstrate similar (compounds 3b, matically converted to 3D models. Each 3D structure was then minimized using MMFF (Merck Molecular Force Field) (compound in neutral form). Then, to each minimized MMFF structure (neutral form), quantum mechanics calculations were run as follows: Equilibrium Geometry; Density Functional, B3LYP, 6-31G*; vacuum; in neutral form; no unpaired electrons.

Cystine depletion levels for the compounds are expressed in Table 4 as a percent relative to the cystine depletion achieved by cysteamine (c.f. cysteamine 100%) at a similar concentration.

Vortex® scatter plots (generated from Dotmatics®) were used to graphically represent the relationship between the sulfur-nitrogen distance and the extent of cystine depletion for the compounds. As shown in FIG. 1, high levels of cystine depletion are observed for compounds having a sulfur-nitrogen distance of about 3.6 to 4.7 Å, and in particular, about 4.1 Å.

Unless indicated (by the term "Abs"), relative stereochemistry is shown in Table 4.

TABLE 4

| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
| F,F-piperidine-SH | 42694 | 4.2 | 20 | <50 | — | — |
| cyclohexane NH$_2$/SH | 42693 | 3.1 | 110 | >90 | — | — |
| cyclohexane NH$_2$/SH | 42692 | 3.1 | 100 | >90 | — | — |
| cyclopentane H$_2$N/SH | 42691 | 5.3 | — | 50-90 | — | — |
| piperidine ester SH | 42690 | 4.1 | — | — | — | — |
| piperidine ester SH | 42689 | 4.1 | — | — | — | — |
| piperidine HS/NH | 42618 | 4.7 | 49 | — | — | — |

TABLE 4-continued

| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
| | 42617 | 4 | 101 | 50-90 | — | <25 |
| | 42616 | 4 | 79 | 50-90 | — | <25 |
| | 42615 | 4.7 | 106 | <50 | — | <25 |
| | 42614 | 4.7 | 117 | — | — | <25 |
| | 42613 | 4.1 | 109 | >90 | — | <25 |
| | 42612 | 4.2 | 98 | — | — | — |
| | 42611 | 5.9 | 55 | >90 | — | <25 |
| | 42610 | 3.1 | 91 | >90 | — | — |
| | 42609 | 4.7 | 17 | — | — | — |
| | 42494 | 4.6 | 88 | 50-90 | — | <25 |

TABLE 4-continued

| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
| ethyl 3-mercaptopiperidine-3-carboxylate | 42493 | 4.1 | 74 | 50-90 | — | <25 |
| trans-4-mercaptocyclohexanamine | 42492 | 6.2 | — | <50 | — | — |
| cis-4-mercaptocyclohexanamine | 42491 | 5.1 | — | <50 | — | <25 |
| trans-3-mercaptocyclobutanamine | 42460 | 4.7 | 111 | 50-90 | — | <25 |
| 1-isopropylpiperidine-4-thiol | 42458 | 4.7 | 91 | >90 | — | — |
| cis-3-mercaptocyclobutanamine | 42457 | 3.8 | 108 | 50-90 | — | <25 |
| 1-ethylpiperidine-4-thiol | 42391 | 4.7 | 60 | >90 | — | — |
| quinuclidine-4-thiol | 42389 | 4.5 | 36 | 50-90 | — | <25 |

TABLE 4-continued

| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
| HS—[3-methyl-piperidine] | 42388 | 4.1 | 97 | >90 | — | <25 |
| [azepane-SH] | 42345 | 3.4 | 50 | >90 | — | <25 |
| [bis-tropane disulfide] | 42344 | 4.7 | 38 | — | — | — |
| [bis-N-methylpyrrolidine disulfide] | 42343 | 3.8 | 84 | — | — | — |
| [bis-N-methylpyrrolidine disulfide, stereoisomer] | 42342 | 3.8 | 91 | — | — | — |
| [4-methyl-4-mercapto-piperidine] | 42341 | 4.7 | 81 | <50 | — | <25 |
| [4-mercaptopyridine] | 42338 | 4.6 | — | <50 | — | — |
| [(S)-3-mercaptopiperidine] | 42248 | 4.1 | 103 | >90 | — | <25 |
| [(R)-3-mercaptopiperidine] | 42247 | 4.1 | 96 | >90 | — | <25 |
| [2-pyridylmethanethiol] | 42213 | 3.7 | 0 | >90 | — | >75 |

TABLE 4-continued
| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
|  | 42212 | 3.3 | — | <50 | — | — |
| 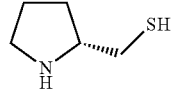 | 42211 | 4.1 | 79 | >90 | — | <25 |
| 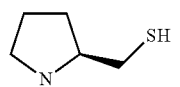 | 42210 | 4.1 | 87 | >90 | — | <25 |
| 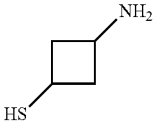 | 42209 | 4.8 | 99 | 50-90 | — | <25 |
| 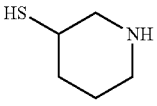 | 42208 | 4.1 | 102 | >90 | — | <25 |
| 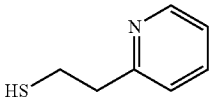 | 42153 | 4.6 | — | — | — | — |
| 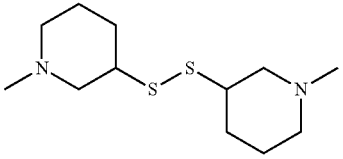 | 42152 | 4.1 | 126 | — | — | — |
| 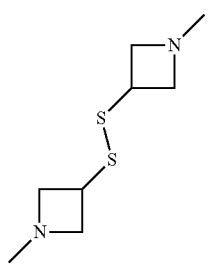 | 42151 | 3.8 | 133 | — | — | — |
| 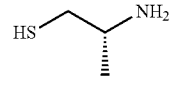 | 42099 | 4.1 | 79 | — | — | 25-75 |
| 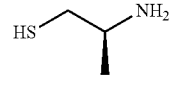 | 42098 | 4.1 | 70 | — | — | <25 |
| 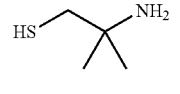 | 42097 | 4.1 | 97 | — | — | — |

TABLE 4-continued
| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
|  | 41448 | 3.1 | 55 | — | — | 25-75 |
| 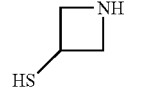 | 41446 | 3.7 | 82 | — | — | <25 |
| 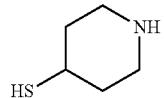 | 41188 | 4.7 | 87 | 50-90 | — | <25 |
| 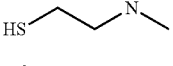 | 18781 | 4.1 | 92 | — | — | <25 |
| 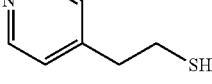 | 17522 | 6.9 | 6 | — | <4000 | <25 |
| 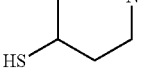 | 17521 | 4.7 | 79 | 50-90 | 4000-9000 | <25 |
| 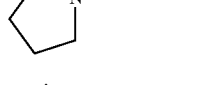 | 17518 | 4.1 | 99 | — | >9000 | <25 |
| 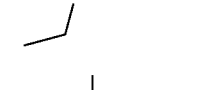 | 17517 | 4.1 | 98 | — | >9000 | <25 |
|  | 17515 | 4.1 | 97 | — | 4000-9000 | <25 |
|  | 17333 | 4.1 | 104 | — | 4000-9000 | <25 |
|  | 17330 | 3.2 | — | — | 4000-9000 | 25-75 |
| 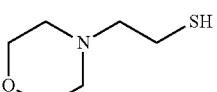 | 17329 | 5.2 | 36 | — | <4000 | <25 |
| 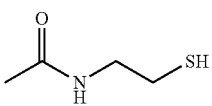 | 17328 | 4.1 | 13 | — | <4000 | <25 |
|  | 17287 | 4.1 | — | — | <4000 | <25 |

TABLE 4-continued

| Compound | Cmpd. No. | S-N Dist. (Å) | Cystine Depletion (%) | Cystine Reactivity Assay (30° C.) (%) Mean Value | Cystine Reactivity Assay (RT) (RFU) Mean Value | ADO Metabolism Assay (%) Mean Value |
|---|---|---|---|---|---|---|
| 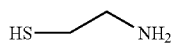 | 1585 | 4.1 | 100 | >90 | 4000-9000 | >75 |
| 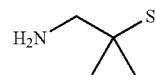 | 18782 | 4.1 | 32 | — | <4000 | <25 |

Example 5

Activity of Compounds

Cystine depletion levels for each of the compounds in Table 5 are expressed as a percent relative to the cystine depletion achieved by cysteamine (c.f. cysteamine 100%) at a similar concentration.

Unless indicated (by the term "Abs"), relative stereochemistry is shown in Table 5.

TABLE 5

| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| 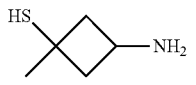 | 152071 | 70 | — | — |
| 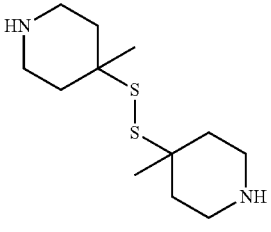 [SMILES: CC1(SSC2(C)CCNCC2)CCNCC1] | 151272 | 11 | — | — |
| 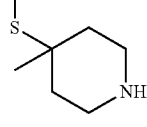 | 151271 | 27 | — | — |
| 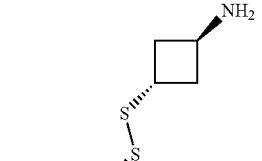 | 151270 | 3 | — | — |

TABLE 5-continued

| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| (3-methyl-3-sulfanyl-piperidine, one enantiomer) | 151182 | 59 | 50-90 | — |
| (3-methyl-3-sulfanyl-piperidine, other enantiomer) | 151181 | 69 | 50-90 | — |
| (3-methyl-3-sulfanyl-pyrrolidine) | 150731 | 58 | >90 | — |
| (3-(hydroxymethyl)-3-sulfanyl-piperidine) | 150730 | 14 | >90 | <25 |
| (4,4-difluoro-2-(sulfanylmethyl)-pyrrolidine) | 149611 | 27 | >90 | — |
| (3-amino-1-hydroxy-1-(sulfanylmethyl)-cyclobutane) | 149610 | 15 | <50 | <25 |
| (trans-3-(methylamino)-cyclobutane-1-thiol) | 149609 | 50 | <50 | <25 |
| (cis-3-(methylamino)-cyclobutane-1-thiol) | 149608 | 55 | <50 | <25 |
| (4,4-difluoro-2-(sulfanylmethyl)-pyrrolidine, enantiomer) | 149607 | 17 | >90 | — |

TABLE 5-continued
| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| 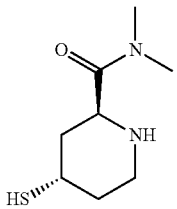 | 145696 | 32 | >90 | <25 |
| 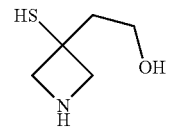 | 145695 | 0 | >90 | <25 |
| 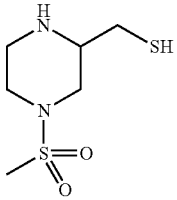 | 145694 | 0 | >90 | <25 |
| 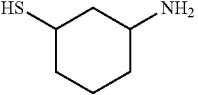 | 145693 | 81 | 50-90 | <25 |
| 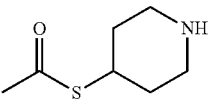 | 145692 | 75 | — | — |
| 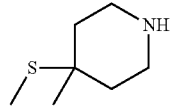 | 145691 | 0 | — | — |
| 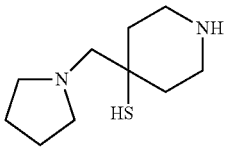 [SMILES: SC1(CN2CCCC2)CCNCC1] | 145611 | 9 | <50 | <25 |
| 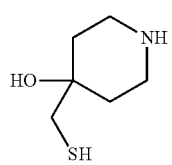 | 145610 | 11 | <50 | <25 |
| 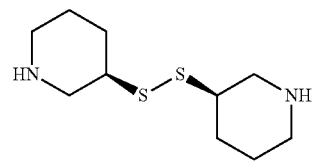 [SMILES: C1CNC[C@H](SS[C@@H]2CCCNC2)C1] | 145609 | 121 | — | <25 |

TABLE 5-continued

| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| HS-CH2-(2-piperidinyl), one stereoisomer | 145592 | 156 | >90 | — |
| (3-morpholinyl)-CH2-SH | 145591 | 61 | 50-90 | <25 |
| HS-CH2-(2-piperidinyl), other stereoisomer | 145590 | 104 | >90 | <25 |
| CH3C(O)S-CH2CH2-NH2 | 145589 | 70 | 50-90 | <25 |
| HS-CH2-(3-piperidinyl) | 145588 | 31 | >90 | <25 |
| HS-CH2-(3-aminocyclobutyl) | 145587 | 13 | >90 | <25 |
| HS-CH2-(4-piperidinyl) | 145586 | 21 | 50-90 | <25 |
| HS-CH2-(3-azetidinyl) | 145585 | 11 | >90 | — |
| 4-mercapto-1-tert-butylpiperidine | 145584 | 0 | >90 | <25 |

TABLE 5-continued
| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| 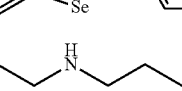 | 145566 | 16 | <50 | <25 |
| 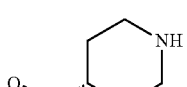 | 145565 | 31 | — | — |
| 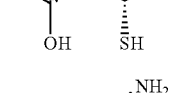 | 145564 | 36 | >90 | 25-75 |
| 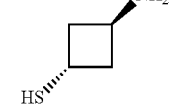 | 145232 | 16 | <50 | <25 |
| 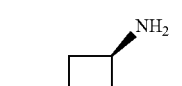 | 42460 | 78 | 50-90 | — |
|  | 42457 | 77 | 50-90 | — |
|  | 42388 | 63 | >90 | <25 |
| 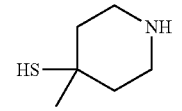 | 42341 | 83 | <50 | — |
|  | 42210 | 89 | >90 | — |
| 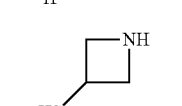 | 41446 | 82 | >90 | <25 |
| 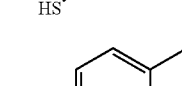 | 2415 | 14 | — | — |

TABLE 5-continued

| Compound | Cmpd. No. | Cystine Depletion (%) Mean Value | Cystine Reactivity Assay (30° C.) (%) Mean Value | ADO Metabolism Assay (%) Mean Value |
|---|---|---|---|---|
| (structure) | 2403 | 19 | <50 | <25 |
| (structure) | 1176 | 10 | <50 | <25 |
| (structure) | 1141 | 0 | <50 | — |
| (structure) | 981 | 25 | <50 | <25 |
| (structure) | 653 | 23 | <50 | <25 |

Example 6

Dimethyl Sulfide (DMS) Detection in Rat Whole Blood Following Oral Compound Administration Male Sprague Dawley (SD) rats (200-250 g) were housed in cages under a 12 hour light/dark cycle with free access to food and water. Temperature and humidity were controlled according to UK Home Office regulations. For oral (po) administration, test compounds were formulated in water at a concentration of 30 mg/mL, to provide a dose of 150 mg/kg when administered orally in a 5 mL/kg dosing volume. Following compound or water (vehicle) administration to rats (n=15 per compound), terminal blood samples (>5 mL) were taken by cardiac puncture under $CO_2$ at defined time-points post oral dosing (pre-dose, 0.25 hour, 0.5 hour, 1 hour and 2 hour). Blood was placed in sealed heparinized Eppendorf tubes on wet ice and stored at 4° C. prior to analyzing DMS levels by gas chromatography (GC).

For each sample of rat blood, 1 mL was added to an evacuated 20 mL GC-Headspace vial containing tetrahydrofuran (THF) internal standard. Headspace vials were sealed with a crimp cap and septum (to prevent the vaporization of volatile sulfur compounds into the open air) and thoroughly vortex mixed. All samples were processed using gas chromatography to measure DMS levels. In short, sulfur containing compounds were thermally liberated into the gas carrier stream and injected (1 μL) into the gas chromatography column (30 m×0.32 mm DB-624 1.8 μm). Under these conditions, the retention time for dimethyl sulfide (DMS) and THF internal standard were approximately 1.83 minutes and 3.82 minutes respectively.

For each analyzed blood sample, the ratio of DMS peak area to THF peak area was calculated. For the DMS calibration curve and assay linearity checks, this ratio was graphically plotted against the concentration of reference DMS standards (blank, 60 nM, 180 nM, 360 nM, 600 nM, 1200 nM, 1800 nM and 3000 nM). The concentration of DMS in each blood sample was calculated from the equation produced by this plot by linear regression analysis. The results are shown in Table 6. The lower limit of detection was 60 nM and a value of <60 indicates no DMS peak was detected in the sample chromatogram. Advantageously, the tested compounds produced reduced levels of DMS compared to cysteamine, suggesting that these compounds have reduced unpleasant side effects (e.g., halitosis) compared to cysteamine therapy.

TABLE 6

| Compound | Cmpd. No. | Dose (mg/kg) po | Mean DMS levels (nM) ± STD | | | | |
|---|---|---|---|---|---|---|---|
| | | | Pre-Dose | Time 0.25 hr | Time 0.5 hr | Time 1 hr | Time 2 hr |
| HS-CH₂CH₂-NH₂ | 1585 | 150 | <60 | 641 ± 324 | 1097 ± 418 | 1162 ± 373 | 1437 ± 334 |
| (4-methyl-4-mercaptopiperidine) | 42341 | 150 | <60 | <60 | <60 | <60 | <60 |
| (2-mercaptomethyl pyrrolidine) | 42210 | 150 | <60 | <60 | No data | <60 | <60 |
| (4-mercaptopiperidine) | 41188 | 150 | <60 | <60 | No data | <60 | <60 |
| (3-mercaptoazetidine) | 41446 | 150 | <60 | <60 | No data | <60 | <60 |
| (2-methyl-2-aminopropane-1-thiol) | 18782 | 150 | <60 | <60 | No data | <60 | <60 |

Example 7

Glutamate-Induced Neuronal Excitotoxicity Assay

The ability of test compounds to inhibit glutamate-induced excitotoxicity (neuroprotection) in St-HdhQ$^{111/111}$ cells was determined by incubating compounds with cells for 60 min at 33° C., 95% (v:v) air/5% (v:v) $CO_2$ in Dulbecco's Modified Eagle Media. Following this, excitotoxicity was induced by the addition of 6 mM L-glutamate for 24 hours. Cell viability was assessed by measuring ATP levels using a luminescent-based CellTitre Glo assay (Promega). Compound neuroprotection (% cell survival) was expressed as a % of the effect recorded with 100 μM cysteamine (denoted as 100% cell survival). Advantageously, the tested compounds resulted in high levels of cell survival (e.g., at least 50% cell survival when expressed as a % of the effect for 100 μM cysteamine), including levels of cell survival highly similar to that of cysteamine (e.g., at least 80% cell survival when expressed as a % of the effect for 100 μM cysteamine), suggesting that these compounds have similar neuroprotection levels as compared to cysteamine therapy.

TABLE 7

| Compound/ Compound No. | HdhQ$^{111/111}$ cell % survival (mean ± STD) | |
|---|---|---|
| | Test Conc. 100 μM | Test Conc. 10 μM |
| 151182 | 85 ± 11 | 1 ± 5 |
| 151181 | 90 ± 9 | 3 ± 8 |

TABLE 7-continued

| Compound/ Compound No. | HdhQ$^{111/111}$ cell % survival (mean ± STD) | |
|---|---|---|
| | Test Conc. 100 μM | Test Conc. 10 μM |
| 149611 | 102 ± 13 | 35 ± 13 |
| 149607 | 98 ± 12 | 32 ± 9 |
| 145695 | 74 ± 10 | 8 ± 10 |
| 145611 | 94 ± 8 | 24 ± 13 |
| 145610 | 87 ± 10 | 11 ± 8 |
| 145592 | 88 ± 8 | 17 ± 10 |
| 145590 | 90 ± 11 | 14 ± 7 |
| 145588 | 98 ± 5 | 9 ± 9 |
| 145587 | 97 ± 7 | 52 ± 9 |
| 145586 | 89 ± 9 | 9 ± 6 |
| 145585 | 100 ± 9 | 13 ± 10 |

TABLE 7-continued

| Compound/Compound No. | HdhQ¹¹¹/¹¹¹ cell % survival (mean ± STD) | |
|---|---|---|
| | Test Conc. 100 μM | Test Conc. 10 μM |
| 145158 | 86 ± 10 | 3 ± 7 |
| 145154 | 93 ± 9 | 13 ± 13 |
| 145153 | 95 ± 6 | 11 ± 11 |
| 42693 | 77 ± 9 | 80 ± 10 |
| 42692 | 71 ± 5 | 82 ± 4 |
| 42617 | 89 ± 7 | 7 ± 10 |
| 42616 | 56 ± 7 | 5 ± 7 |
| 42614 | 59 ± 12 | 2 ± 6 |
| 42610 | 77 ± 8 | 19 ± 6 |
| 42493 | 87 ± 10 | 6 ± 10 |
| 42460 | 95 ± 9 | 3 ± 5 |
| 42457 | 91 ± 6 | 6 ± 5 |
| 42388 | 91 ± 5 | 5 ± 6 |
| 42341 | 55 ± 21 | 1 ± 10 |
| 42248 | 81 ± 6 | 2 ± 7 |
| 42247 | 84 ± 13 | 5 ± 8 |
| 42211 | 84 ± 19 | 2 ± 9 |
| 42210 | 105 ± 8 | 7 ± 6 |
| 41446 | 101 ± 11 | 6 ± 9 |
| 41188 | 105 ± 11 | 20 ± 6 |
| 1585 | 105 ± 13 | 20 ± 6 |
| 145694 | 15 ± 15 | 2 ± 10 |
| 145156 | 16 ± 7 | 1 ± 6 |
| 42494 | 28 ± 17 | 0 ± 7 |

Numerous modifications and variations in the invention as set forth in the above illustrative examples are expected to occur to those skilled in the art. Consequently only such limitations as appear in the appended claims should be placed on the invention.

What is claimed:

1. A compound having the following structure or a disulfide thereof:

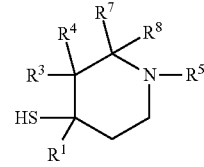

wherein $R^1$ is $C_{1-5}$alkyl; and
$R^3$, $R^4$, $R^5$, $R^7$, and $R^8$ are independently selected from the group consisting of H and $C_{1-5}$ alkyl.

2. A compound having the following structure or a disulfide thereof:

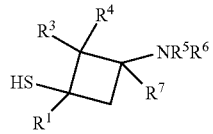

wherein $R^1$, $R^3$, $R^4$, $R^5$, $R^6$, and $R^7$ are independently selected from the group consisting of H and $C_{1-5}$alkyl.

* * * * *